(12) United States Patent
Tamaru et al.

(10) Patent No.: US 9,957,538 B2
(45) Date of Patent: May 1, 2018

(54) SOFT BIOMASS DECOMPOSITION METHOD

(71) Applicant: NATIONAL UNIVERSITY CORPORATION MIE UNIVERSITY, Mie (JP)

(72) Inventors: Yutaka Tamaru, Mie (JP); Takeshi Katsuyama, Tokyo (JP)

(73) Assignee: NATIONAL UNIVERSITY CORPORATION MIE UNIVERSITY, Mie (JP)

( * ) Notice: Subject to any disclaimer, the term of this patent is extended or adjusted under 35 U.S.C. 154(b) by 30 days.

(21) Appl. No.: 14/378,172

(22) PCT Filed: Jan. 29, 2013

(86) PCT No.: PCT/JP2013/051883
§ 371 (c)(1),
(2) Date: Aug. 12, 2014

(87) PCT Pub. No.: WO2013/121875
PCT Pub. Date: Aug. 22, 2013

(65) Prior Publication Data
US 2015/0010960 A1 Jan. 8, 2015

(30) Foreign Application Priority Data
Feb. 17, 2012 (WO) ............... PCT/JP2012/053744

(51) Int. Cl.
C12P 19/14 (2006.01)
C12P 19/02 (2006.01)
C12N 9/42 (2006.01)
C12P 7/14 (2006.01)
C12P 7/16 (2006.01)
C12P 7/10 (2006.01)

(52) U.S. Cl.
CPC ............ *C12P 19/14* (2013.01); *C12N 9/2434* (2013.01); *C12N 9/2437* (2013.01); *C12P 7/10* (2013.01); *C12P 7/14* (2013.01); *C12P 7/16* (2013.01); *C12P 19/02* (2013.01); *C12Y 302/01004* (2013.01); *C12Y 302/01091* (2013.01); *Y02E 50/16* (2013.01)

(58) Field of Classification Search
None
See application file for complete search history.

(56) References Cited

U.S. PATENT DOCUMENTS

2010/0035320 A1 2/2010 Blanchard et al.
2012/0196338 A1 8/2012 Blanchard et al.

FOREIGN PATENT DOCUMENTS

| JP | 2007-053050 | 3/2007 |
| JP | 2008-161125 | 7/2008 |
| JP | 2011-182675 | 9/2011 |
| JP | 2011-529345 | 12/2011 |
| WO | WO2009108941 | * 9/2009 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Accession O65986. Aug. 1, 1998.*
Accession Q9XD99. Nov. 1, 1999.*
Accession Q9RGE8. May 1, 2000.*
Yang et al. Metab Eng. Nov. 2015;32:39-4.*
Jeon et al. Metab Eng. Nov. 2015;32:39-48.*
English language translation of International Preliminary Report on Patentability issued in PCT/JP2013/051883, dated Aug. 28, 2014.
Tamaru et al., "Genome Sequence of the Cellulosome-Producing Mesophilic Organism *Clostridium cellulovorans* 743B", Journal of Bacteriology, vol. 192, No. 3, pp. 901-902, 2010.
Sleat et al., "Isolation and Characterization of an Anaerobic, Cellulolytic Bacterium, *Clostridium cellulovorans* sp. nov", Applied and Environmental Microbiology, vol. 48, No. 1, pp. 88-93, 1984.
Arai et al., "Properties of cellulosomal family 9 cellulases from *Clostridium cellulovorans*", Appl. Microbiol. Biotechnol., vol. 71, pp. 654-660, 2006.
Murashima et al., "Synergistic Effects on Crystalline Cellulose Degradation between Cellulosomal Cellulases from *Clostridium cellulovorans*", Journal of Bacteriology, vol. 184, No. 18, pp. 5088-5095, 2002.
Liu et al., "Properteis of exgS, a gene for a major subunit of the *Clostridium cellulovorans* cellulosome", Gene, vol. 211, pp. 39-47, 1998.
Tamaru et al., "Three Surface Layer Homology Domains at the N Terminus of the *Clostridium cellulovorans* Major Cellulosomal Subunit EngE", Journal of Bacteriology, vol. 181, No. 10, pp. 3270-3276,1999.
Database Genbank, Accession No. AF132735: "Clostridium cellulovorans endoglucanase K (engK), hydrophobic protein A (hbpA), endoglucanase L (engL), mannanase A (manA), endoglucanase M (engM), endoglucananse N (engN), and transposase (trp) genes, complete cds; and malate permease (mln) gene, partial cds", Oct. 24, 2000, http://www.ncbi.nlm.nih.gov/nuccore/AF132735.

(Continued)

*Primary Examiner* — Christian Fronda
(74) *Attorney, Agent, or Firm* — Greenblum & Bernstein, P.L.C.

(57) ABSTRACT

An object of the present invention is to provide a soft biomass decomposition method, a production method for a target substance from soft biomass, and an enzyme or group of enzymes for decomposing soft biomass. Provided is a soft biomass decomposition method, including a step of bringing an enzyme selected from specific exocellulase, endocellulase, and processive endocellulase into contact with soft biomass such as bagasse and rice straw. Also provided is a production method for a target substance from soft biomass by incorporating the soft biomass decomposition method as a step. Further provided is an enzyme or group of enzymes for decomposing soft biomass selected from specific exocellulase, endocellulase, and processive endocellulase.

2 Claims, 6 Drawing Sheets

(56) References Cited

OTHER PUBLICATIONS

Tamaru et al., "A Large Gene Cluster for the *Clostridium cellulovorans* Cellulosome", *Journal of Bacteriology*, vol. 182, No. 20, pp. 5906-5910, Oct. 2000.
Tamaru, "Genome Kaiseki to Biomass Kanzen Riyo eno Oyo" *Chemical Engineering*, vol. 56, No. 6, pp. 438-445, 2011.
Ueda et al., "Soft Biomass Kanzen Toka no Shin Bio Gijutsu <Soft Biomass o Kanzen Bunkai-Toka suru Atarashii Biseibutsu Mae Shori Gijutsu>", *Haikan Gijutsu*, vol. 52, No. 7, pp. 1-6, 2010.
International Search Report of PCT/JP2013/051883 dated Apr. 23, 2013, along with an English language translation.
Australian Office Action issued with respect to Application No. 2013219650, dated Sep. 28, 2017.
Tamaru et al., "Comparison of the mesophilic cellulosome-producing Clostridium cellulovorans genome with other cellulosome-related clostridial genomes", Microbial Biotechnology, 2011, 4(1):64-73.
Han et al., "Effect of carbon source on the cellulosomal subpopulations of Clostridium cellulovorans", Microbiology, 2005, 151(Pt5):1491-1497.

\* cited by examiner

A.

B.

C.

SOFT BIOMASS DECOMPOSITION METHOD

TECHNICAL FIELD

The present invention relates to a soft biomass decomposition method. More particularly, the present invention relates to a soft biomass decomposition method, including a step of bringing an enzyme into contact with soft biomass, and an enzyme or group of enzymes for decomposing soft biomass.

BACKGROUND ART

There have been a wide variety of attempts to develop technologies for producing a useful substance such as alcohols such as ethanol and butanol, and lactic acid by using as a raw material woody biomass such as wooden chips or soft biomass such as rice straw and bagasse.

Production of the useful substance from those biomass raw materials requires decomposition of the biomass raw materials to sugar and subsequent fermentation of the obtained sugar. In recent years, the biomass raw materials have been saccharified mainly by enzymes. However, the biomass raw materials include various impurities other than cellulose, and therefore, there is a problem in that the enzymes hardly act on the biomass raw materials. In this context, in order to enhance saccharification efficiency, there are developed various methods involving, as pretreatment, subjecting the biomass raw materials to steam treatment using dilute sulfuric acid, hot compressed water, or the like, treating the biomass raw materials with a supercritical ammonia fluid, and the like (for example, see Patent Literature 1).

In addition, there have been attempts to develop microorganisms useful for decomposition of the biomass raw materials.

For example, Patent Literature 2 discloses a method of improving decomposition capability for cellulose contained in the biomass raw materials by expressing a chimeric enzyme in which endocellulase (GH5) derived from *Acidothermus cellulolyticus* is fused with cellobiohydrolase (CBH) derived from *Trichoderma reesei* in *Trichoderma reesei* producing cellulase as a host.

Further, while it is necessary to conduct a saccharification step and a fermentation step independently for obtaining the useful substance such as ethanol from the biomass, there have been attempts to develop technologies capable of conducting these steps at once.

For example, Patent Literature 3 discloses providing a microorganism capable of directly hydrolyzing and fermenting lignocellulose-based biomass by enhancing activity of cellulase by modification. As one of the cellulases whose activity is to be enhanced, there are given hydrolase identified in *Clostridium phytofermentans* and the like, and a polynucleotide encoding the hydrolase and the like are disclosed.

In addition, Patent Literature 4 discloses a technology for expressing a chimeric protein including some cellulase derived from a microorganism not producing a cellulosome and a dockrin domain derived from a microorganism producing a cellulosome in yeast with a view to forming an artificial cellulosome. However, an artificial cellulosome is not formed in yeast in this literature.

The cellulosome is an enzyme complex formed of two components, i.e., a scaffolding protein (CbpA) not exhibiting enzyme activity and a group of cellulosomal enzymes. The scaffolding protein (CbpA) has a cellulose-binding domain (CBD), Cohesin domains, and Surface Layer Homology (SLH) domains. The group of cellulosomal enzymes have a dockerin domain to bind to the Cohesin domain of the scaffold protein (CbpA). Those components bind to each other to form the enzyme complex (cellulosome), and thereby, cellulose and hemicellulose can be degraded efficiently.

It can be said that microorganisms forming cellulosomes are useful microorganisms for decomposition and fermentation of the biomass raw materials. As such microorganisms, *Clostridium cellulovorans* (hereinafter sometimes referred to as *C. cellulovorans*)) and the like are known.

*Clostridium cellulovorans* (*C. cellulovorans*) is a gram-positive obligatory anaerobic mesophilic bacterium. The inventors of the present invention have confirmed that *Clostridium cellulovorans* (*C. cellulovorans*) has a genome size about 1 Mb larger than those of *Clostridium cellulolyticum* and *Clostridium thermocellum* belonging to the same genus *Clostridium* (see, for example, Non Patent Literature 1).

Moreover, Non Patent Literature 2 discloses that *Clostridium cellulovorans* (*C. cellulovorans*) produced useful substances such as acetate and butyrate by fermenting a test sample containing cellobiose and the like and also suggests that ethanol was produced.

Further, as a group of cellulosomal enzymes derived from *Clostridium cellulovorans* (*C. cellulovorans*), Endoglucanase E (EngE), which is endocellulase of Glycosyl Hydrolase family 5 (GH5), Endoglucanase K (EngK), which is processive endocellulase of Glycosyl Hydrolase family 9 (GH9), Endoglucanase H (EngH), which is processive endocellulase of Glycosyl Hydrolase family 9 (GH9), Exoglucanase S (ExgS), which is exocellulase of Glycosyl Hydrolase family 48 (GH48), and the like are known.

Of those, it is disclosed that EngK exhibits high activity for insoluble cellulose (see, for example, Non Patent Literature 3). In addition, it is also disclosed that each of a mixture of ExgS and EngE, a mixture of ExgS and EngH, and a mixture of EngE and EngH has specific activity for crystalline cellulose as compared to EngE, EngH, or ExgS alone (see, for example, Non Patent Literature 4).

As described above, it is suggested that *Clostridium cellulovorans* (*C. cellulovorans*) or an enzyme or group of enzymes derived from this microorganism are useful for decomposition and fermentation of the biomass.

However, the biomass such as woody biomass and soft biomass includes various impurities other than cellulose in accordance with the type of the biomass, unlike test samples, insoluble cellulose, crystalline cellulose, and the like. Therefore, direct decomposition and fermentation of the actual biomass (bagasse, rice straw, and the like) are not always possible.

Accordingly, there is a demand for a method enabling direct decomposition and fermentation of the actual biomass without the need to conduct a step of pretreatment and the like as well as the need to conduct the saccharification step and fermentation step independently. There is also a demand for a microorganism, an enzyme or group of enzymes, and the like capable of decomposing and fermenting the actual biomass in accordance with its type.

CITATION LIST

Patent Literature

[PTL 1] JP 2008-161125 A
[PTL 2] JP 2007-53050 A

[PTL 3] JP 2011-529345 A
[PTL 4] JP 2011-182675 A

Non Patent Literature

[NPL 1] Y. Tamaru et al., J. Bacteriol., 192, 901-902 (2010)
[NPL 2] ROBERT SLEAT et al., Applied and Environmental Microbiology., July 1984, p. 88-93
[NPL 3] TakamitsuArai et al., Appl Microbiol Biotechnol 2006, 71 p. 654-660
[NPL 4] Koichiro MURASHIMA et al., Journal of Bacteriology September 2002, p. 5088-5095

SUMMARY OF INVENTION

Technical Problem

It is an object of the present invention to provide a method that enables appropriate decomposition of soft biomass, particularly actual biomass such as bagasse or rice straw in accordance with the type of the biomass. It is another object of the present invention to provide a method of producing a useful substance such as ethanol as a target substance by incorporating the decomposition method.

It is still another object of the present invention to provide an enzyme or a combination of enzymes (group of enzymes) capable of acting effectively in accordance with the type of the soft biomass.

Solution to Problem

As a result of diligent study aimed at achieving the objects described above, the inventors of the present invention have found that bringing an enzyme selected from specific exocellulase, endocellulase, and processive endocellulase into contact with soft biomass such as bagasse and rice straw enables direct decomposition of the actual biomass. Thus, the finding is proposed as a soft biomass decomposition method of the present invention. Moreover, the inventors have found that a useful substance such as ethanol can be produced as a target substance from soft biomass such as bagasse and rice straw by incorporating the decomposition method.

In addition, the inventors have further found an enzyme or group of enzymes capable of acting effectively in accordance with the type of soft biomass such as bagasse and rice straw.

That is, the present invention relates to a soft biomass decomposition method, a production method for a target substance from soft biomass, and an enzyme or group of enzymes for decomposing soft biomass as described in the following items (1) to (20).

(1) A soft biomass decomposition method, the method comprising a step of bringing an enzyme into contact with soft biomass, the enzyme comprising an exocellulase having an amino acid sequence having 90% or more identity to an amino acid sequence set forth in SEQ ID NO: 2.
(2) A soft biomass decomposition method according to the above-mentioned item (1), wherein the exocellulase comprises ExgS.
(3) A soft biomass decomposition method according to the above-mentioned item (1) or (2), the method further comprising a step of bringing an enzyme into contact with soft biomass, the enzyme comprising an endocellulase having an amino acid sequence having 90% or more identity to an amino acid sequence set forth in SEQ ID NO: 4.
(4) A soft biomass decomposition method according to the above-mentioned item (3), wherein the endocellulase comprises EngE.
(5) A soft biomass decomposition method according to any one of the above-mentioned items (1) to (4), wherein the soft biomass comprises rice straw.
(6) A soft biomass decomposition method according to any one of the above-mentioned items (1) to (4), the method further comprising a step of bringing an enzyme into contact with soft biomass, the enzyme comprising a processive endocellulase having an amino acid sequence having 90% or more identity to an amino acid sequence set forth in SEQ ID NO: 6.
(7) A soft biomass decomposition method according to the above-mentioned item (6), wherein the processive endocellulase comprises EngK.
(8) A soft biomass decomposition method according to the above-mentioned item (6) or (7), wherein the soft biomass comprises bagasse.
(9) A soft biomass decomposition method according to any one of the above-mentioned items (1) to (8), wherein the step of bringing an enzyme into contact with soft biomass is conducted by bringing a microorganism producing any one of the following enzymes 1) to 3) into contact with the soft biomass:
1) exocellulase;
2) exocellulase and endocellulase; and
3) exocellulase, endocellulase, and processive endocellulase.
(10) A soft biomass decomposition method according to the above-mentioned item (9), wherein the microorganism comprises *Clostridium cellulovorans*.
(11) A production method for a target substance from soft biomass, the method comprising a step of decomposing soft biomass by the soft biomass decomposition method according to any one of the above-mentioned items (1) to (10).
(12) A production method for a target substance from soft biomass according to the above-mentioned item (11), wherein the target substance comprises any one or more kinds selected from ethanol, acetic acid, butyric acid, lactic acid, formic acid, and hydrogen.
(13) An enzyme or group of enzymes for decomposing soft biomass, comprising any one or more kinds of the following enzymes 1) to 3):
1) an exocellulase having an amino acid sequence having 90% or more identity to an amino acid sequence set forth in SEQ ID NO: 2;
2) an endocellulase having an amino acid sequence having 90% or more identity to an amino acid sequence set forth in SEQ ID NO: 4; and
3) a processive endocellulase having an amino acid sequence having 90% or more identity to an amino acid sequence set forth in SEQ ID NO: 6.
(14) An enzyme or group of enzymes for decomposing soft biomass according to the above-mentioned item (13), wherein the exocellulase comprises ExgS, the endocellulase comprises EngE, and the processive endocellulase comprises EngK.
(15) A group of enzymes for decomposing soft biomass according to the above-mentioned item (13) or (14), comprising at least the following enzymes 1) and 2):

1) an exocellulase having an amino acid sequence having 90% or more identity to an amino acid sequence set forth in SEQ ID NO: 2; and
2) an endocellulase having an amino acid sequence having 90% or more identity to an amino acid sequence set forth in SEQ ID NO: 4.
(16) A group of enzymes for decomposing soft biomass according to the above-mentioned item (15), wherein the soft biomass comprises rice straw.
(17) A group of enzymes for decomposing soft biomass according to the above-mentioned item (13) or (14), comprising at least the following enzymes 1) to 3):
1) an exocellulase having an amino acid sequence having 90% or more identity to an amino acid sequence set forth in SEQ ID NO: 2; and
2) an endocellulase having an amino acid sequence having 90% or more identity to an amino acid sequence set forth in SEQ ID NO: 4; and
3) a processive endocellulase having an amino acid sequence having 90% or more identity to an amino acid sequence set forth in SEQ ID NO: 6.
(18) A group of enzymes for decomposing soft biomass according to the above-mentioned item (17), wherein the soft biomass comprises bagasse.
(19) A group of enzymes for decomposing soft biomass according to the above-mentioned item (13) or (14), comprising at least the following enzymes 1) and 2):
1) an exocellulase having an amino acid sequence having 90% or more identity to an amino acid sequence set forth in SEQ ID NO: 2; and
2) a processive endocellulase having an amino acid sequence having 90% or more identity to an amino acid sequence set forth in SEQ ID NO: 6.
(20) A group of enzymes for decomposing soft biomass according to the above-mentioned item (13) or (14), comprising at least the following enzymes 1) and 2) at a rate of from 5:95 to 95:5:
1) an exocellulase having an amino acid sequence having 90% or more identity to an amino acid sequence set forth in SEQ ID NO: 2; and
2) a processive endocellulase having an amino acid sequence having 90% or more identity to an amino acid sequence set forth in SEQ ID NO: 6.

Advantageous Effects of Invention

According to one embodiment of the present invention, it is possible to directly degrade soft biomass by a simple procedure without pretreatment and the like and produce a useful substance such as ethanol. Further, according to one embodiment of the present invention, it is also possible to provide an enzyme or group of enzymes capable of acting usefully in accordance with the type of soft biomass.

DESCRIPTION OF EMBODIMENTS

Figure 1:
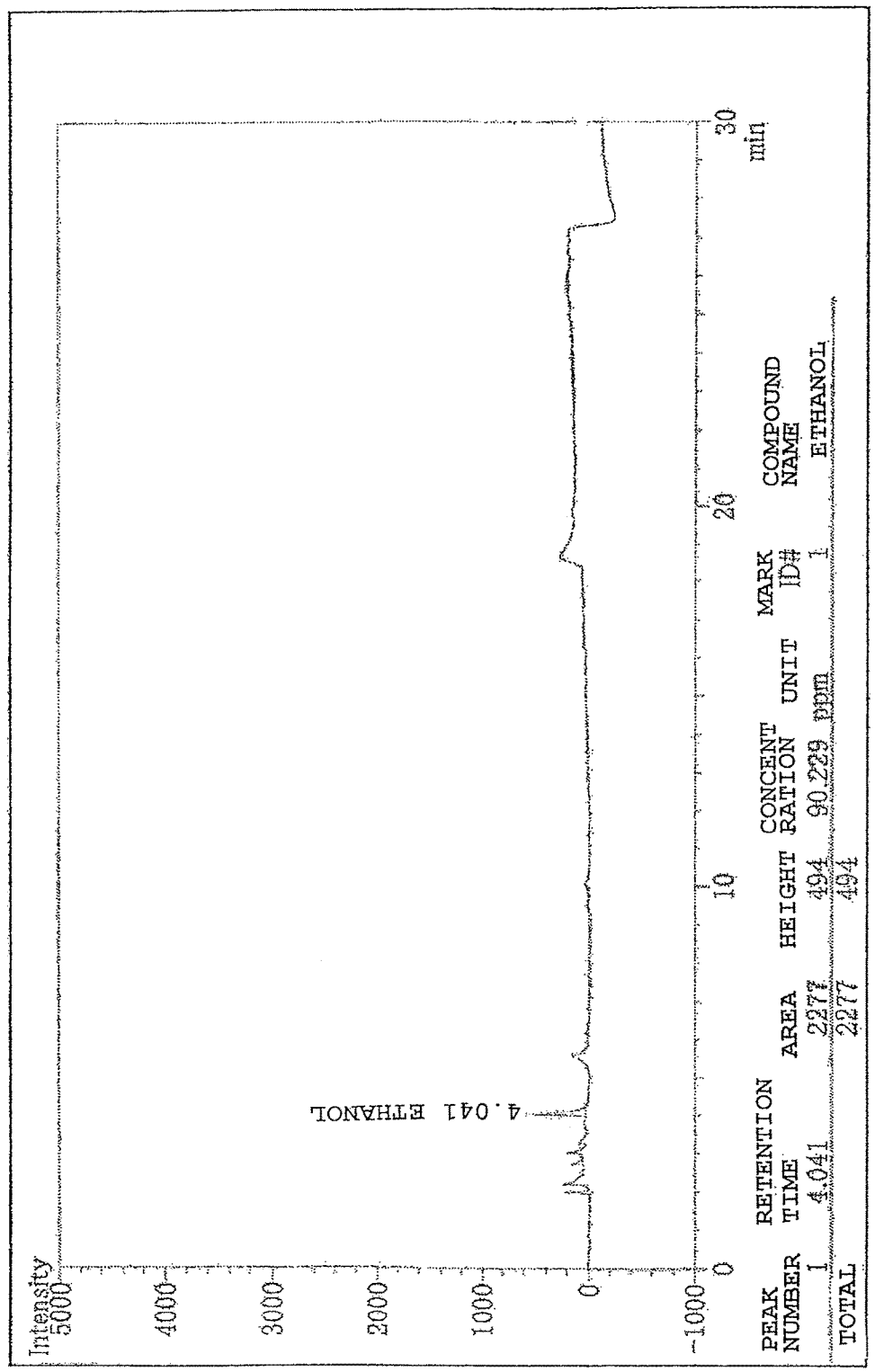
FIG. 1 is a chart showing a result of target substance production using soft biomass as a raw material in *C. cellulovorans* (Example 1).

The "soft biomass decomposition method" in the present invention refers to a method of decomposing cellulose contained in soft biomass heretofore known such as rice straw and bagasse by an enzyme.
The "soft biomass decomposition method" of the present invention is a "method of decomposing soft biomass" including a step of bringing "exocellulase having an amino acid sequence having 90% or more identity to the amino acid sequence set forth in SEQ ID NO: 2" into contact with soft biomass, and may include other steps.
Now, the "amino acid sequence having 90% or more identity" in the "exocellulase having an amino acid sequence having 90% or more identity to the amino acid sequence set forth in SEQ ID NO: 2" means an amino acid sequence in which 90% or more, preferably 95% or more, more preferably 98% or more, still more preferably 99% or more of amino acid residues are identical to those of the amino acid sequence set forth in SEQ ID NO: 2 when the amino acid sequence set forth in SEQ ID NO: 2 and the amino acid sequence other than the amino acid sequence set forth in SEQ ID NO: 2 are compared to each other by aligning these sequences so that the largest possible number of amino acid residues match each other. Herein, in alignment of the amino acid sequences, a gap may be included to provide the maximum identity.
Moreover, while the "amino acid sequence having 90% or more identity" is an amino acid sequence having 90% or more identity, the "amino acid sequence having identity" of the present invention may also include an amino acid sequence having 80% or more identity and an amino acid sequence having 85% or more identity. In particular, the "amino acid sequence having 90% or more identity" is preferred as the amino acid sequence.
Further, the "amino acid sequence having 90% or more identity" may include an "amino acid sequence in which one or several amino acids are deleted, substituted, or added." A Preferred example of such amino acid sequence is an amino acid sequence in which 1, 2, 3, 4, 5, 6, 7, 8, 9, or 10 amino acids are deleted, substituted, or added as compared to the amino acid sequence set forth in SEQ ID NO: 2 serving as a standard. Further preferred examples include an amino acid sequence in which 1, 2, 3, 4, or 5 amino acids are deleted, substituted, or added.
As an enzyme having such amino acid sequence, there is given ExgS of Glycosyl Hydrolase family 48 (GH48) having the amino acid sequence set forth in SEQ ID NO: 2 derived from *Clostridium cellulovorans* (*C. cellulovorans*), for example, as the "exocellulase having an amino acid sequence having 90% or more identity to the amino acid sequence set forth in SEQ ID NO: 2".
The ExgS is encoded by the base sequence set forth in SEQ ID NO: 1. In the present invention, the "exocellulase having an amino acid sequence having 90% or more identity to the amino acid sequence set forth in SEQ ID NO: 2" can be identified also by a base sequence. Examples of the base sequence encoding the "exocellulase having an amino acid sequence having 90% or more identity to the amino acid sequence set forth in SEQ ID NO: 2" of the present invention also include a base sequence having 80% or more identity, a base sequence having 85% or more identity, a base sequence having 90% or more identity, and a base sequence having 95% or more identity to the base sequence set forth in SEQ ID NO: 1 as long as they are base sequences encoding the exocellulase.

Further, the "soft biomass decomposition method" in the present invention may be a "soft biomass decomposition method" including a step of bringing "endocellulase having an amino acid sequence having 90% or more identity to the amino acid sequence set forth in SEQ ID NO: 4" into contact with soft biomass, and may include other steps.

Herein, the "amino acid sequence having 90% or more identity" in the "endocellulase having an amino acid sequence having 90% or more identity to the amino acid sequence set forth in SEQ ID NO: 4" means an amino acid sequence in which 90% or more, preferably 95% or more, more preferably 98% or more, still more preferably 99% or more of amino acid residues are identical to those of the amino acid sequence set forth in SEQ ID NO: 4 when the amino acid sequence set forth in SEQ ID NO: 4 and the amino acid sequence other than the amino acid sequence set forth in SEQ ID NO: 4 are compared to each other by aligning these sequences so that the largest possible number of amino acid residues match each other. Herein, in alignment of the amino acid sequences, a gap may be included to provide the maximum identity.

Moreover, while the "amino acid sequence having 90% or more identity" may be an amino acid sequence having 90% or more identity, the "amino acid sequence having identity" of the present invention may also include an amino acid sequence having 80% or more identity and an amino acid sequence having 85% or more identity. In particular, the "amino acid sequence having 90% or more identity" is preferred as the amino acid sequence.

Further, the "amino acid sequence having 90% or more identity" may include an "amino acid sequence in which one or several amino acids are deleted, substituted, or added." A preferred example of such amino acid sequence is an amino acid sequence in which 1, 2, 3, 4, 5, 6, 7, 8, 9, or 10 amino acids are deleted, substituted, or added as compared to the amino acid sequence set forth in SEQ ID NO: 4 serving as a standard. A more preferred example thereof is an amino acid sequence in which 1, 2, 3, 4, or 5 amino acids are deleted, substituted, or added.

As an enzyme having such amino acid sequence, there is given EngE of Glycosyl Hydrolase family 5 (GH5) having the amino acid sequence set forth in SEQ ID NO: 4 derived from *Clostridium cellulovorans* (*C. cellulovorans*), for example, as the "endocellulase having an amino acid sequence having 90% or more identity to the amino acid sequence set forth in SEQ ID NO: 4".

EngE is encoded by the base sequence set forth in SEQ ID NO: 3. In the present invention, the "endocellulase having an amino acid sequence having 90% or more identity to the amino acid sequence set forth in SEQ ID NO: 4" can be identified also by a base sequence. Examples of the base sequence encoding the "endocellulase having an amino acid sequence having 90% or more identity to the amino acid sequence set forth in SEQ ID NO: 4" of the present invention also include a base sequence having 80% or more identity, a base sequence having 85% or more identity, a base sequence having 90% or more identity, and a base sequence having 95% or more identity to the base sequence set forth in SEQ ID NO: 3 as long as they are base sequences encoding the endocellulase.

Further, the "soft biomass decomposition method" in the present invention may be a "soft biomass decomposition method" including a step of bringing "processive endocellulase having an amino acid sequence having 90% or more identity to the amino acid sequence set forth in SEQ ID NO: 6" into contact with soft biomass, and may include other steps.

Now, the "amino acid sequence having 90% or more identity" in the "processive endocellulase having an amino acid sequence having 90% or more identity to the amino acid sequence set forth in SEQ ID NO: 6" means an amino acid sequence in which 90% or more, preferably 95% or more, more preferably 98% or more, still more preferably 99% or more of amino acid residues are identical to those of the amino acid sequence set forth in SEQ ID NO: 6 when the amino acid sequence set forth in SEQ ID NO: 6 and the amino acid sequence other than the amino acid sequence set forth in SEQ ID NO: 6 are compared to each other by aligning these sequences so that the largest possible number of amino acid residues match each other. Herein, in alignment of the amino acid sequences, a gap may be included to provide the maximum identity.

Moreover, while the "amino acid sequence having 90% or more identity" may be an amino acid sequence having 90% or more identity, the "amino acid sequence having identity" of the present invention may also include an amino acid sequence having 80% or more identity and an amino acid sequence having 85% or more identity. In particular, the "amino acid sequence having 90% or more identity" is preferred as the amino acid sequence.

Further, the "amino acid sequence having 90% or more identity" may include an "amino acid sequence in which one or several amino acids are deleted, substituted, or added." A preferred example of such amino acid sequence is an amino acid sequence in which 1, 2, 3, 4, 5, 6, 7, 8, 9, or 10 amino acids are deleted, substituted, or added as compared to the amino acid sequence set forth in SEQ ID NO: 6 serving as a standard. A more preferred example thereof is an amino acid sequence in which 1, 2, 3, 4, or 5 amino acids are deleted, substituted, or added.

As an enzyme having such amino acid sequence, there is given EngK of Glycosyl Hydrolase family 9 (GH9) having the amino acid sequence set forth in SEQ ID NO: 6 derived from *Clostridium cellulovorans* (*C. cellulovorans*), for example, as the "processive endocellulase having an amino acid sequence having 90% or more identity to the amino acid sequence set forth in SEQ ID NO: 6".

EngK is encoded by the base sequence set forth in SEQ ID NO: 5. In the present invention, the "processive endocellulase having an amino acid sequence having 90% or more identity to the amino acid sequence set forth in SEQ ID NO: 6" can be identified also by a base sequence. Examples of the base sequence encoding the "processive endocellulase having an amino acid sequence having 90% or more identity to the amino acid sequence set forth in SEQ ID NO: 6" of the present invention also include a base sequence having 80% or more identity, a base sequence having 85% or more identity, a base sequence having 90% or more identity, and a base sequence having 95% or more identity to the base sequence set forth in SEQ ID NO: 5 as long as they are base sequences encoding the processive endocellulase.

In the "soft biomass decomposition method" of the present invention, the "bringing an enzyme into contact with soft biomass" refers to bringing an enzyme into contact with soft biomass so that the enzyme can act to degrade the soft biomass.

Now, the "soft biomass" in the present invention refers to soft biomass such as rice straw, bagasse, wheat straw, rice husk, erianthus, miscanthus, napier grass, sorghum and corn stover as it is, those prepared by suspending the soft biomass as it is or after cut into an appropriate size in a solvent such as water or a buffer (soft biomass suspension), or the like.

Further, the "soft biomass" in the present invention also includes a medium including rice straw as a substrate and a medium including bagasse as a substrate prepared by the same manner as in Examples of the present invention through addition of components such as $K_2HPO_4 \cdot 3H_2O$, $NH_4Cl$, KCl, $MgSO_4 \cdot 7H_2O$, L-cysteine hydrochloride monohydrate, Trypton, a yeast extract, and a trace metal solution to the soft biomass or the soft biomass suspension.

The method of bringing an enzyme into contact with soft biomass only needs to be a method of bringing an enzyme into contact with soft biomass so that the enzyme can act to degrade the soft biomass, and any methods heretofore known can be employed.

For example, in the case where the "soft biomass" of the present invention is soft biomass as it is or soft biomass simply after cut into an appropriate size, there are given: a method of immersing the soft biomass in the enzyme or a solution containing the enzyme; a method of injecting the enzyme or a solution containing the enzyme into the soft biomass by injection or the like; a method of sprinkling the enzyme or a solution containing the enzyme on the soft biomass; and the like. In addition, pressure treatment such as depressurization or pressurization may be conducted as required to allow the enzyme to permeate the soft biomass, while the enzyme is brought into contact with the soft biomass or after the enzyme is brought into contact with the soft biomass.

In the case where the "soft biomass" of the present invention is the medium including rice straw as a substrate, the medium including bagasse as a substrate, or the like, there are given: a method of adding the enzyme or a solution containing the enzyme to the medium; a method of mixing the medium and the enzyme or a solution containing the enzyme; and the like.

It should be noted that the method of "bringing an enzyme into contact with soft biomass" includes not only the methods of bringing the enzyme or a solution containing the enzyme but also methods of bringing a microorganism producing the enzyme or group of enzymes into contact with the soft biomass by the same methods as described above.

Those methods of "bringing an enzyme into contact with soft biomass" are the same whether the enzyme is the "exocellulase having an amino acid sequence having 90% or more identity to the amino acid sequence set forth in SEQ ID NO: 2", the "endocellulase having an amino acid sequence having 90% or more identity to the amino acid sequence set forth in SEQ ID NO: 4", or the "processive endocellulase having an amino acid sequence having 90% or more identity to the amino acid sequence set forth in SEQ ID NO: 6". Those methods are the same even when those enzymes are brought into contact with the soft biomass as a group of enzymes.

The "soft biomass decomposition method" of the present invention may include a step of bringing the "exocellulase having an amino acid sequence having 90% or more identity to the amino acid sequence set forth in SEQ ID NO: 2" and the "endocellulase having an amino acid sequence having 90% or more identity to the amino acid sequence set forth in SEQ ID NO: 4" into contact with the soft biomass.

In this step, the enzymes only need to be brought into contact with the soft biomass at an optimum rate for the decomposition. For example, the "exocellulase having an amino acid sequence having 90% or more identity to the amino acid sequence set forth in SEQ ID NO: 2" and the "endocellulase having an amino acid sequence having 90% or more identity to the amino acid sequence set forth in SEQ ID NO: 4" may be brought into contact at a rate of 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5, or the like.

Those enzymes may be brought into contact with the soft biomass by the methods as recited above. The bringing those enzymes into contact with the soft biomass may be conducted by bringing the "exocellulase having an amino acid sequence having 90% or more identity to the amino acid sequence set forth in SEQ ID NO: 2" into contact with the soft biomass, and then, bringing the "endocellulase having an amino acid sequence having 90% or more identity to the amino acid sequence set forth in SEQ ID NO: 4" into contact with the soft biomass. In this case, the enzymes may be brought into contact with the soft biomass in reverse order.

Alternatively, the "exocellulase having an amino acid sequence having 90% or more identity to the amino acid sequence set forth in SEQ ID NO: 2" and the "endocellulase having an amino acid sequence having 90% or more identity to the amino acid sequence set forth in SEQ ID NO: 4" may be brought into contact with the soft biomass at one time.

Alternatively, soft biomass with which the "exocellulase having an amino acid sequence having 90% or more identity to the amino acid sequence set forth in SEQ ID NO: 2" has been brought into contact and soft biomass with which the "endocellulase having an amino acid sequence having 90% or more identity to the amino acid sequence set forth in SEQ ID NO: 4" has been brought into contact may be separately prepared and then mixed with each other.

Examples of those contact methods include the case of bringing each of a microorganism producing the "exocellulase having an amino acid sequence having 90% or more identity to the amino acid sequence set forth in SEQ ID NO: 2" and a microorganism producing the "endocellulase having an amino acid sequence having 90% or more identity to the amino acid sequence set forth in SEQ ID NO: 4" into contact with the soft biomass.

Further, the case of bringing a microorganism producing the "exocellulase having an amino acid sequence having 90% or more identity to the amino acid sequence set forth in SEQ ID NO: 2" and the "endocellulase having an amino acid sequence having 90% or more identity to the amino acid sequence set forth in SEQ ID NO: 4" into contact with the soft biomass is also included.

In the "soft biomass decomposition method" including the step of bringing the "exocellulase having an amino acid sequence having 90% or more identity to the amino acid sequence set forth in SEQ ID NO: 2" and the "endocellulase having an amino acid sequence having 90% or more identity to the amino acid sequence set forth in SEQ ID NO: 4" into contact with the soft biomass, the soft biomass with which each enzyme or group of enzymes are brought into contact may be any soft biomass heretofore known, but is particularly preferably rice straw.

Further, the "soft biomass decomposition method" of the present invention may include a step of bringing the "exocellulase having an amino acid sequence having 90% or more identity to the amino acid sequence set forth in SEQ ID NO: 2", the "endocellulase having an amino acid sequence having 90% or more identity to the amino acid sequence set forth in SEQ ID NO: 4", and the "processive endocellulase having an amino acid sequence having 90% or more identity to the amino acid sequence set forth in SEQ ID NO: 6" into contact with the soft biomass. In this step, the enzymes only need to be brought into contact with the soft biomass at an optimum rate for the decomposition.

Those enzymes may be brought into contact with the soft biomass by the methods as recited above. The bringing those enzymes into contact with the soft biomass may be conducted by bringing the "exocellulase having an amino acid sequence having 90% or more identity to the amino acid sequence set forth in SEQ ID NO: 2" into contact with the soft biomass, then bringing the "endocellulase having an amino acid sequence having 90% or more identity to the amino acid sequence set forth in SEQ ID NO: 4" into contact with the soft biomass, and then bringing the "processive endocellulase having an amino acid sequence having 90% or more identity to the amino acid sequence set forth in SEQ ID NO: 6" into contact with the soft biomass. In this case, the enzymes may be brought into contact with the soft biomass in any order.

Alternatively, the "exocellulase having an amino acid sequence having 90% or more identity to the amino acid sequence set forth in SEQ ID NO: 2", the "endocellulase having an amino acid sequence having 90% or more identity to the amino acid sequence set forth in SEQ ID NO: 4", and the "processive endocellulase having an amino acid sequence having 90% or more identity to the amino acid sequence set forth in SEQ ID NO: 6" may be brought into contact with the soft biomass at one time.

Alternatively, soft biomass with which the "exocellulase having an amino acid sequence having 90% or more identity to the amino acid sequence set forth in SEQ ID NO: 2" has been brought into contact, soft biomass with which the "endocellulase having an amino acid sequence having 90% or more identity to the amino acid sequence set forth in SEQ ID NO: 4" has been brought into contact, and soft biomass with which the "processive endocellulase having an amino acid sequence having 90% or more identity to the amino acid sequence set forth in SEQ ID NO: 6" has been brought into contact may be separately prepared, and then mixed with each other.

Examples of those contact methods include the case of bringing each of a microorganism producing the "exocellulase having an amino acid sequence having 90% or more identity to the amino acid sequence set forth in SEQ ID NO: 2", a microorganism producing the "endocellulase having an amino acid sequence having 90% or more identity to the amino acid sequence set forth in SEQ ID NO: 4", a microorganism producing the "processive endocellulase having an amino acid sequence having 90% or more identity to the amino acid sequence set forth in SEQ ID NO: 6" into contact with the soft biomass.

Further, examples of those contact methods also include the case of bringing each of a microorganism producing the "exocellulase having an amino acid sequence having 90% or more identity to the amino acid sequence set forth in SEQ ID NO: 2" and the "endocellulase having an amino acid sequence having 90% or more identity to the amino acid sequence set forth in SEQ ID NO: 4", a microorganism producing the "exocellulase having an amino acid sequence having 90% or more identity to the amino acid sequence set forth in SEQ ID NO: 2" and the "processive endocellulase having an amino acid sequence having 90% or more identity to the amino acid sequence set forth in SEQ ID NO: 6", and a microorganism producing the "endocellulase having an amino acid sequence having 90% or more identity to the amino acid sequence set forth in SEQ ID NO: 4" and the "processive endocellulase having an amino acid sequence having 90% or more identity to the amino acid sequence set forth in SEQ ID NO: 6" into contact with the soft biomass.

Further, examples of those contact methods also include the case of bringing a microorganism producing all of the "exocellulase having an amino acid sequence having 90% or more identity to the amino acid sequence set forth in SEQ ID NO: 2", the "endocellulase having an amino acid sequence having 90% or more identity to the amino acid sequence set forth in SEQ ID NO: 4", and the "processive endocellulase having an amino acid sequence having 90% or more identity to the amino acid sequence set forth in SEQ ID NO: 6" into contact with the soft biomass.

In the "soft biomass decomposition method" including the step of bringing the "exocellulase having an amino acid sequence having 90% or more identity to the amino acid sequence set forth in SEQ ID NO: 2", the "endocellulase having an amino acid sequence having 90% or more identity to the amino acid sequence set forth in SEQ ID NO: 4", and the "processive endocellulase having an amino acid sequence having 90% or more identity to the amino acid sequence set forth in SEQ ID NO: 6" into contact with the soft biomass, the soft biomass with which each enzyme or group of enzymes are brought into contact may be any soft biomass heretofore known, but is particularly preferably bagasse.

Further, the "soft biomass decomposition method" of the present invention may include a step of bringing the "exocellulase having an amino acid sequence having 90% or more identity to the amino acid sequence set forth in SEQ ID NO: 2" and the "processive endocellulase having an amino acid sequence having 90% or more identity to the amino acid sequence set forth in SEQ ID NO: 6" into contact with the soft biomass.

In this step, the enzymes only need to be brought into contact with the soft biomass at an optimum rate for the decomposition. For example, the "exocellulase having an amino acid sequence having 90% or more identity to the amino acid sequence set forth in SEQ ID NO: 2" and the "processive endocellulase having an amino acid sequence having 90% or more identity to the amino acid sequence set forth in SEQ ID NO: 6" may be brought into contact at a rate of 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5, or the like.

Those enzymes may be brought into contact with the soft biomass by the methods as recited above. The bringing those enzymes into contact with the soft biomass may be conducted by bringing the "exocellulase having an amino acid sequence having 90% or more identity to the amino acid sequence set forth in SEQ ID NO: 2" into contact with the soft biomass, and then bringing the "processive endocellulase having an amino acid sequence having 90% or more identity to the amino acid sequence set forth in SEQ ID NO: 6" into contact with the soft biomass. In this case, the enzymes may be brought into contact with the soft biomass in reverse order.

Alternatively, the "exocellulase having an amino acid sequence having 90% or more identity to the amino acid sequence set forth in SEQ ID NO: 2" and the "processive endocellulase having an amino acid sequence having 90% or more identity to the amino acid sequence set forth in SEQ ID NO: 6" may be brought into contact with the soft biomass at one time.

Alternatively, soft biomass with which the "exocellulase having an amino acid sequence having 90% or more identity to the amino acid sequence set forth in SEQ ID NO: 2" has been brought into contact and soft biomass with which the "processive endocellulase having an amino acid sequence having 90% or more identity to the amino acid sequence set forth in SEQ ID NO: 6" has been brought into contact may be separately prepared and then mixed with each other.

In those contact methods, the case of bringing each of a microorganism producing the "exocellulase having an amino acid sequence having 90% or more identity to the amino acid sequence set forth in SEQ ID NO: 2" and a microorganism producing the "processive endocellulase having an amino acid sequence having 90% or more identity to the amino acid sequence set forth in SEQ ID NO: 6" into contact with the soft biomass is included.

Further, the case of bringing a microorganism producing the "exocellulase having an amino acid sequence having 90% or more identity to the amino acid sequence set forth in SEQ ID NO: 2" and the "processive endocellulase having an amino acid sequence having 90% or more identity to the amino acid sequence set forth in SEQ ID NO: 6" into contact with the soft biomass is also included.

In the "soft biomass decomposition method" including the step of bringing the "exocellulase having an amino acid sequence having 90% or more identity to the amino acid sequence set forth in SEQ ID NO: 2" and the "processive endocellulase having an amino acid sequence having 90% or more identity to the amino acid sequence set forth in SEQ ID NO: 6" into contact with the soft biomass, the soft biomass with which each enzyme or a group of enzymes are brought into contact may be any soft biomass heretofore known such as rice straw and bagasse.

In the soft biomass decomposition method of the present invention including bringing a microorganism producing any one of the following enzymes 1) to 3) into contact with the soft biomass, the microorganism may be any microorganism heretofore known as long as the microorganism produces any one of the following enzymes 1) to 3), but is preferably a microorganism capable of forming a cellulosome. *Clostridium cellulovorans* (*C. cellulovorans*), which is a microorganism capable of forming a cellulosome, is particularly preferred.

It should be noted that, in the following enzymes 1) to 3), the "exocellulase" refers to the "exocellulase having an amino acid sequence having 90% or more identity to the amino acid sequence set forth in SEQ ID NO: 2", the "endocellulase" refers to the "endocellulase having an amino acid sequence having 90% or more identity to the amino acid sequence set forth in SEQ ID NO: 4", and the "processive endocellulase" refers to the "processive endocellulase having an amino acid sequence having 90% or more identity to the amino acid sequence set forth in SEQ ID NO: 6".
1) exocellulase
2) exocellulase and endocellulase
3) exocellulase, endocellulase, and processive endocellulase A "production method for a target substance from soft biomass" of the present invention only needs to include a step of decomposing soft biomass by the "soft biomass decomposition method" of the present invention, and may include other steps. The "production method for a target substance from soft biomass" of the present invention is preferably a method enabling direct production of the target substance by decomposition of the soft biomass and subsequent fermentation of sugar or the like obtained by the decomposition.

The "target substance" in the present invention may be any of compounds or the like as long as it is obtained through the "soft biomass decomposition method" of the present invention. Examples of the "target substance" in the present invention may include ethanol, acetic acid, butyric acid, lactic acid, formic acid, and hydrogen.

The "enzyme or group of enzymes for decomposing soft biomass" of the present invention refers to an enzyme or group of enzymes capable of decomposing soft biomass such as rice straw and bagasse, and examples thereof include an enzyme or group of enzymes decomposing cellulose contained in the soft biomass into glucose or the like.

The "enzyme or group of enzymes" of the present invention only needs to be an enzyme or group of enzymes including any one or more kinds of the following enzymes 1) to 3):
1) exocellulase having an amino acid sequence having 90% or more identity to the amino acid sequence set forth in SEQ ID NO: 2;
2) endocellulase having an amino acid sequence having 90% or more identity to the amino acid sequence set forth in SEQ ID NO: 4; and
3) processive endocellulase having an amino acid sequence having 90% or more identity to the amino acid sequence set forth in SEQ ID NO: 6.

Of those, as the "exocellulase having an amino acid sequence having 90% or more identity to the amino acid sequence set forth in SEQ ID NO: 2", there are given ExgS of Glycosyl Hydrolase family 48 (GH48) having the amino acid sequence set forth in SEQ ID NO: 2 derived from *Clostridium cellulovorans* (*C. cellulovorans*) and the like, for example.

Moreover, as the "endocellulase having an amino acid sequence having 90% or more identity to the amino acid sequence set forth in SEQ ID NO: 4", there are given EngE of Glycosyl Hydrolase family 5 (GH5) having the amino acid sequence set forth in SEQ ID NO: 4 derived from *Clostridium cellulovorans* (*C. cellulovorans*) and the like, for example.

Further, as the "processive endocellulase having an amino acid sequence having 90% or more identity to the amino acid sequence set forth in SEQ ID NO: 6", there are given EngK of Glycosyl Hydrolase family 9 (GH9) having the amino acid sequence set forth in SEQ ID NO: 6 derived from *Clostridium cellulovorans* (*C. cellulovorans*) and the like, for example.

Of those, examples of the "group of enzymes" for decomposing soft biomass include a group of enzymes including at least the above-mentioned enzymes 1) and 2). In the group of enzymes, each of the enzymes 1) and 2) only needs to be included at an optimum rate for the decomposition of the soft biomass. For example, the "exocellulase having an amino acid sequence having 90% or more identity to the amino acid sequence set forth in SEQ ID NO: 2" as the enzyme 1) and the "endocellulase having an amino acid sequence having 90% or more identity to the amino acid sequence set forth in SEQ ID NO: 4" as the enzyme 2) may be included at a rate of 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5, or the like. The soft biomass to be degraded by such "group of enzymes" may be any soft biomass heretofore known, but is particularly preferably rice straw.

Moreover, examples of the "group of enzymes" for decomposing soft biomass include a group of enzymes including at least the above-mentioned enzymes 1) to 3). In the group of enzymes, each of the enzymes 1) to 3) may be included at an optimum rate for the decomposition of the soft biomass. The soft biomass to be degraded by such "group of enzymes" may be any soft biomass heretofore known, but is particularly preferably bagasse.

Further, examples of the "group of enzymes" for decomposing soft biomass include a group of enzymes including at least the above-mentioned enzymes 1) and 3). In the group of enzymes, each of the enzymes 1) and 3) only needs to be included at an optimum rate for the decomposition of the soft biomass. For example, the "exocellulase having an amino acid sequence having 90% or more identity to the amino acid sequence set forth in SEQ ID NO: 2" as the enzyme 1) and the "processive endocellulase having an amino acid sequence having 90% or more identity to the amino acid sequence set forth in SEQ ID NO: 6" as the enzyme 3) may be included at a rate of 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5, or the like. The soft biomass to be degraded by such "group of enzymes" may be any soft biomass heretofore known such as rice straw and bagasse.

It should be noted that the "group of enzymes" particularly desirably forms cellulosomes at the time of acting to degrade soft biomass such as rice straw and bagasse.

The present invention is hereinafter described in more detail byway of Examples of the present invention, but the present invention is not limited to Examples and various modifications may be made without departing from the technical concept of the present invention.

EXAMPLE 1

<Production of Target Substance Using Soft Biomass as Raw Material in *C. cellulovorans*>
1. Medium
1) Medium Including Rice Straw as a Substrate A medium including 0.5% (w/v) rice straw as a substrate was prepared through the following steps (1) to (4) with reference to Non Patent Literature 2.
(1) 1 g of $K_2HPO_4.3H_2O$, 1 g of $NH_4Cl$, 0.5 g of KCl, 0.5 g of $MgSO_4.7H_2O$, 0.15 g of L-cysteine hydrochloride monohydrate, 0.5 g of Trypton, 0.5 g of a yeast extract, 5 g of rice straw, 20 ml of a trace metal solution, and 0.001 g of resazurin were dissolved in distilled water to adjust the volume to 1 L.
(2) After the step (1), the pH was adjusted to 7 by 4 M NaOH, and $CO_2$ gas was bubbled therein until resazurin was reduced (the color of the medium changed from red to yellow) while being boiled.
(3) After the step (2), the flask was plugged and sterilized in an autoclave.
(4) After the step (3), 0.05 ml of a mixed solution of 10% (wt/vol) $Na_2CO_3$ and 1.5% (w/v) $Na_2S.9H_2O$ was added thereto to adjust the pH to 7.2. Thus, a medium including 0.5% (w/v) rice straw as a substrate was obtained.
2) Preculture Medium In the preparation method for a medium including rice straw as a substrate in the above-mentioned section 1), the steps (1) to (3) were conducted without rice straw, and then, cellobiose was added so that the final concentration was 0.3% (w/v). Thus, a preculture medium including cellobiose was prepared.
2. Preparation of Sample
1) *Clostridium cellulovorans* (*C. cellulovorans*) was precultured in the preculture medium obtained in the above-mentioned section 1.2) at 37° C. for 1 day.
2) A part of the medium after the culture in the above-mentioned section 1) was put in the medium including rice straw as a substrate obtained in the above-mentioned section 1. 1), and further, static culture was performed at 37° C. for 1 month.
3) After the culture in the above-mentioned section 2), centrifugal separation (15,000×g, 15 minutes, 4° C.) was conducted to recover culture supernatant, followed by filtration using a filter Millex-LH (0.45 μm). 1 μL of the resultant was subjected to gas chromatography.

As the column for gas chromatography, RT (trademark)-Q-BOND (manufactured by Restek Corporation) was used, and the concentrations of ethanol and butanol were measured at an SPL temperature of 250° C., a column temperature of 150° C., an FID temperature of 250° C. with flowing N2 as a carrier gas at a linear velocity of 30 cm/sec.

As a result, in *C. cellulovorans*, ethanol was detected at a concentration of 90.229 ppm in the medium including rice straw as a substrate, as shown in FIG. 1. Accordingly, the result indicated that ethanol could be produced directly from rice straw, which was actual biomass, by decomposing and fermenting the rice straw by *C. cellulovorans*.

EXAMPLE 2

<Identification of Enzyme or Group of Enzymes Acting Appropriately in Accordance with Substrate>
1. Medium
1) Medium Including Bagasse as a Substrate A medium including 0.5% (w/v) bagasse as a substrate was prepared by the same preparation method as that for the medium including rice straw as a substrate in Example 1 except that 5 g of bagasse were used as the substrate instead of the rice straw.
2) Medium Including Rice Straw as a Substrate A medium including 0.5% (w/v) rice straw as a substrate was prepared by the same method as in Example 1.
3) Preculture Medium A preculture medium including 0.3% (w/v) cellobiose was prepared by the same method as in Example 1.
2. Preparation of Sample
1) *Clostridium cellulovorans* (*C. cellulovorans*) was precultured in the preculture medium obtained in the above-mentioned section 1.3) at 37° C. for 1 day.
2) A part of the medium after the culture in the above-mentioned section 1) was put in the medium including bagasse as a substrate obtained in the above-mentioned section 1. 1) or the medium including rice straw as a substrate obtained in the above-mentioned section 1. 2), and further, static culture was performed at 37° C. for a certain period of time.
3) After the culture in the above-mentioned section 2), centrifugal separation was conducted to recover culture supernatant, and all proteins contained in the culture supernatant were precipitated by an ammonium sulfate precipitation method. After washing, the precipitated proteins were dissolved in Tris-HCl buffer (pH 7.5), and thus, a protein solution was obtained.
4) The protein solution obtained in the above-mentioned section 3) was taken as a supernatant fraction. Further, Avicel (trademark) PH-101 (manufactured by Sigma-Aldrich Co. LLC.) (hereinafter sometimes referred to as Avicel) was added as cellulose to the supernatant fraction, the mixture was incubated at 4° C. for 1 hour, and Avicel and supernatant were separated by centrifugal precipitation. The resultant supernatant was taken as a fraction not adsorbed on cellulose (hereinafter sometimes referred to as non-adsorbed fraction). Further, proteins adsorbed on Avicel were dissolved in SDS-Sample Buffer, which was taken as a fraction adsorbed on cellulose (hereinafter sometimes referred to as adsorbed fraction).

3. SDS-PAGE

Each of the samples (supernatant fraction, fraction not adsorbed on cellulose, and fraction adsorbed on cellulose) prepared in the above-mentioned section 2. was separated by SDS-PAGE, and CBB staining was conducted. The SDS-PAGE and CBB staining were conducted by ordinary methods.

Bands that appeared in a particularly deep color in SDS-PAGE were selected, and bands that appeared in a deep color in both of the adsorbed fractions of bagasse and rice straw (B1, B4, R1, and R2 in FIG. 2), a band that appeared in a remarkably deep color in the adsorbed fraction of bagasse (B2 in FIG. 2), and further, a band that appeared in a deep color almost only in the adsorbed fraction of bagasse (B3 in FIG. 2) were each cut out, and a CBB destaining solution was removed by washing with sterile distilled water.

4. Identification of Protein

The amino acid sequence of the protein contained in each of the bands cut in the above-mentioned section 3. was determined with a high-performance liquid chromatograph-mass spectrometer (LTQ Orbitrap Velos ETD manufactured by Thermo Fisher Scientific K.K.).

The determined amino acid sequence was compared to the genome sequence of C. cellulovorans, and the protein contained in each band was identified. The results are shown in Table 1.

TABLE 1

| Substrate | Bagasse | Rice straw | SEQ ID NO | Protein |
|---|---|---|---|---|
| Sample | B1 | R1 | — | pyruvate ferredoxin/flavodoxin oxidoreductase |
|  | B2 | — | 4 | Glycosyl Hydrolase family 5 (GH5)/Endocellulase (EngE) |
|  | B3 | — | 6 | Glycosyl Hydrolase family 9 (GH9)/Processive endocellulase (EngK) |
|  | B4 | R2 | 2 | Glycosyl Hydrolase family 48 (GH48)/Exocellulase (ExgS) |

5. Analysis Result

B1 and R1 were bands at the same position and identified as including pyruvate ferredoxin/flavodoxin oxidoreductase as a protein. Pyruvate ferredoxin/flavodoxin oxidoreductase is a metabolic enzyme of general anaerobic bacteria used for production of acetic acid and ATP from pyruvic acid.

B2 was identified as including, as a protein, EngE of Glycosyl Hydrolase family 5 (GH5) having the amino acid sequence set forth in SEQ ID NO: 4 in the sequence listing.

EngE is an endocellulase and genome analysis confirmed that EngE was primary endoglucanase present outside the cellulosome gene cluster in the C. cellulovorans genome. Further, the fact that a band at the same position was confirmed for the sample derived from the medium including rice straw as a substrate in FIG. 2 suggested that EngE was likely to be the primary constituent component of the cellulosome.

Moreover, B3 was identified as including, as a protein, EngK of Glycosyl Hydrolase family 9 (GH9) having the amino acid sequence set forth in SEQ ID NO: 6 in the sequence listing.

EngK is a processive endocellulase and genome analysis confirmed that EngK was included in the cellulosome gene cluster in the C. cellulovorans genome. Although EngK has a CBM, the family of the CBM is different from that of CBM of CbpA (CbpA family: CBM3, EngK family: CBM4_9).

Further, B4 and R2 were bands at the same position and identified as including, as a protein, ExgS of Glycosyl Hydrolase family 48 (GH48) having the amino acid sequence set forth in SEQ ID NO: 2 in the sequence listing.

ExgS is an exocellulase and genome analysis confirmed that ExgS was a cellulosomal enzyme included in the cellulosome gene cluster in the C. cellulovorans genome. The fact that ExgS did not have a cellulose-binding module (CBM) suggested that ExgS was recovered in a state in which the CBM of CbpA was adsorbed on Avicel and the dockerin domain of ExgS was bound to the adsorbed cohesin domain of CbpA.

It should be noted that the enzymes are encoded in the order of ExgS, EngH, and then EngK in the cellulosome gene cluster in genome analysis of C. cellulovorans, but in the present system, EngH was not detected.

Accordingly, those results suggested that an exocellulase (ExgS) having the amino acid sequence set forth in SEQ ID NO: 2 and an endocellulase (EngE) having the amino acid sequence set forth in SEQ ID NO: 4 were important for the decomposition of rice straw.

Further, those results suggested that an exocellulase (ExgS) having the amino acid sequence set forth in SEQ ID NO: 2, an endocellulase (EngE) having the amino acid sequence set forth in SEQ ID NO: 4, and a processive endocellulase (EngK) having the amino acid sequence set forth in SEQ ID NO: 6 were important for the decomposition of bagasse.

EXAMPLE 3

<Confirmation-1 of Synergistic Action of Enzymes>

1. Confirmation of Expression of Each of Enzymes BglA, ExgS, and EngK

Recombinant BglA, ExgS, and EngK were each expressed in Escherichia coli (E. coli) serving as a host through the following steps 1) to 5).

1) bglA (SEQ ID NO: 7), exgS (SEQ ID NO: 1), and engK (SEQ ID NO: 5) were each inserted downstream of Trigger factor, which was a solubilizing tag of pCold-TF (Takara Bio Inc.) serving as a vector for low-temperature expression, and gene-transferred to E. coli origami serving as a host for expression.

2) For the gene-transferred E. coli origami obtained in the above-mentioned section 1), colonies to which the genes were transferred respectively were subjected to screening by a colony direct PCR method, and inoculated into a 5-ml LB medium (supplemented with ampicillin (final concentration: 100 μg/ml)).

3) The colonies to which the genes were transferred respectively obtained in the above-mentioned section 2) were each cultured at 37° C. and 180 rpm for 6 hours, and then, 1 ml of the culture solution was inoculated into a 500-ml 2×YT medium (supplemented with ampicillin (final concentration: 100 μg/ml)).

When it reached logarithmic growth phase ($OD_{600}$=0.45 to 0.5), incubation was performed at 15° C. at 180 rpm for 30 minutes, and then, IPTG was added thereto so that the final concentration was 1.0 mM to induce protein expression, followed by incubation at 15° C. at 180 rpm for 24 hours.

4) Each of the bacteria in which protein expression was induced obtained in the above-mentioned section 3) was harvested by centrifugal precipitation (10,000×g, 4° C., 10 minutes), and suspended in 8 ml of a 20 mM phosphate buffer (pH 7.4, 500 mM NaCl, 10 mM imidazole).

The suspension was subjected to sonication for about 300 seconds while cooled with ice so that the temperature did not rise. The suspension was then subjected to centrifugal precipitation (20,000×g, 4° C., 30 minutes) and the supernatant was taken as a soluble fraction. The precipitate was suspended in 8 ml of the same phosphate buffer and the precipitate was subjected to sonication and taken as an insoluble fraction.

5) Each of the fractions obtained in the above-mentioned section 4) was subjected to SDS-PAGE, and CBB staining and immunostaining were used to confirm whether or not the target protein was present.

Figure 3A:
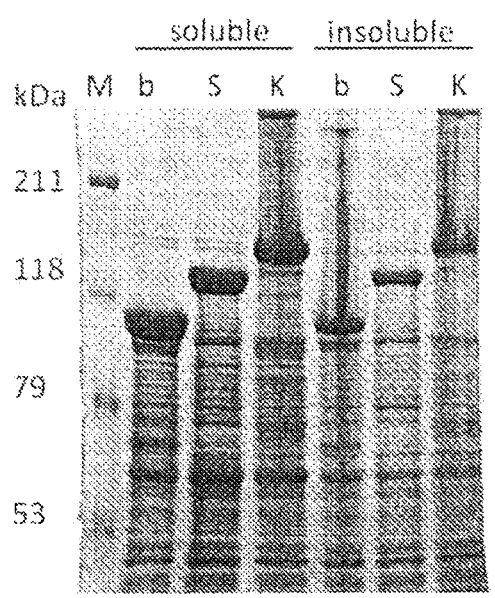
FIG. 3A is an image showing results of CBB staining (Example 3).

As a result, it was confirmed that each of the proteins (BglA, ExgS, or EngK) was expressed in the soluble fraction and the expression level was increased, as shown in FIG. 3A as the result of CBB staining.

Figure 3B:
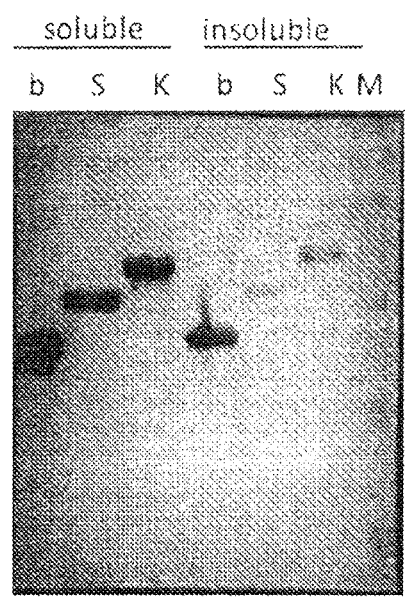
FIG. 3B is an image showing results of western blotting (Example 3).

Further, FIG. 3B shows the result of western blotting for each of the proteins (BglA, ExgS, or EngK) by an ordinary method using an anti-His antibody. As a result, it was confirmed that expression of each of the proteins (BglA, ExgS, or EngK) was suppressed in the insoluble fraction.

2. Measurement of Enzyme Activity of ExgS and EngK

For each of the soluble fractions obtained in the above-mentioned section 1., qualitative enzyme activity was evaluated by the following method 1) or 2).

1) β-Glucosidase activity was evaluated by adding 10 µl of the soluble fraction of each of the proteins (BglA, ExgS, or EngK) to 1 ml of a 10 mM p-nitrophenyl-β-glucoside solution, incubating the mixture at 37° C. for 5 minutes, and then observing the change in color of the solution.

2) Cellulase activity was evaluated as described below.

5% (w/v) phosphoric acid swollen Avicel (acid swollen cellulose: ASC) was added to 490 µl of a 20 mM phosphate buffer (pH 7.4, 500 mM NaCl, 10 mM imidazole) dispensed into a 1.5-ml tube, and enzyme solutions were added thereto as shown in Table 2.

After that, incubation was performed at 37° C. at 180 rpm for 18 hours, and then, the amount of free reducing sugar was measured by a DNS method.

TABLE 2

| tube label | Content(s) | |
|---|---|---|
| b | bglA gene containing E. coli (origami) soluble fraction | 10 µl |
| S | exgS gene containing E. coli (origami) soluble fraction | 10 µl |
| K | engK gene containing E. coli (origami) soluble fraction | 10 µl |
| S | exgS gene containing E. coli (origami) soluble fraction | 5 µl |
| K | engK gene containing E. coli (origami) soluble fraction | 5 µl |
| S + K | exgS gene containing E. coli (origami) soluble fraction | 5 µl |
|  | engK gene containing E. coli (origami) soluble fraction | 5 µl |
| N1 | 20-ml phosphate buffer (pH 7.4) | 10 µl |
| N2 | E. coli (origami) soluble fraction | 10 µl |

Figure 4:
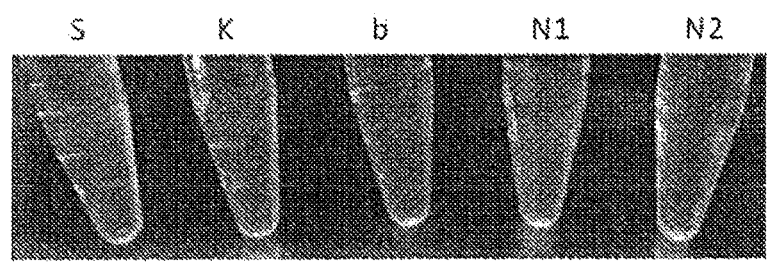
FIG. 4 is an image showing results of qualitative enzyme activity for p-nitrophenyl-β-glucoside (Example 3).

FIG. 4 shows the result of qualitative enzyme activity for p-nitrophenyl-β-glucoside. As a result, only an experimental plot b (one prepared by adding the soluble fraction obtained from E. coli (transformant) to which a bglA gene was transferred) was colored in yellow as shown in FIG. 4, and the β-glucosidase activity was observed only for this transformant.

Figure 5:
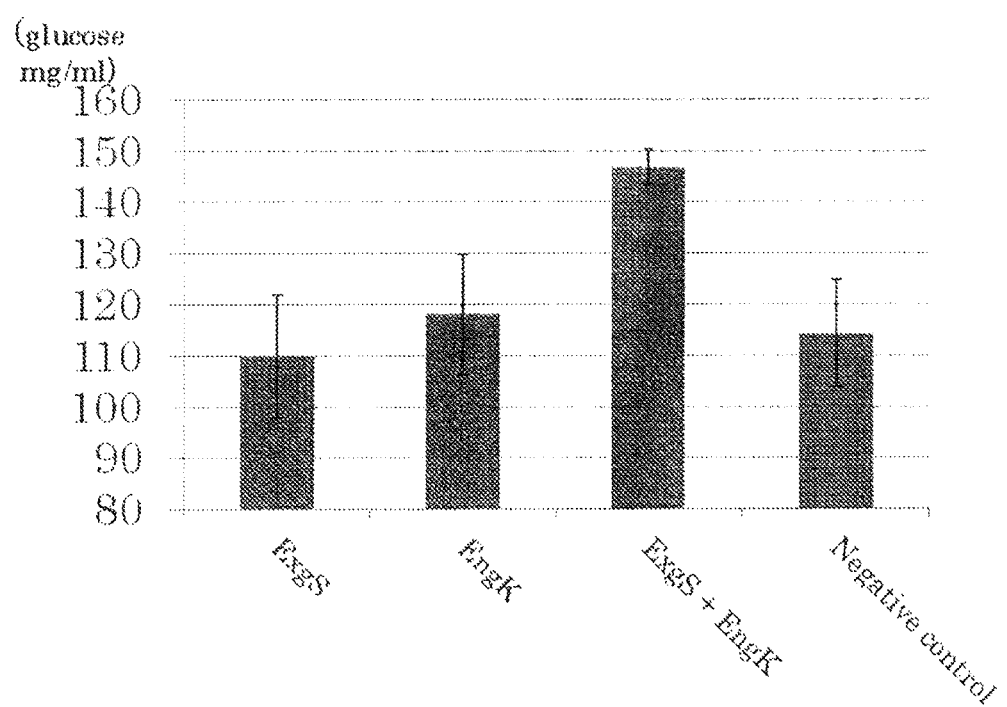
FIG. 5 is a graph showing evaluation results of ASC activity (Example 3).

Further, FIG. 5 shows the evaluation result of ASC activity. As a result, ExgS (GH family 48) alone exhibited substantially no cellulase activity as shown in FIG. 5. In contrast, EngK (GH family 9) alone exhibited extremely low cellulase activity. Further, mixing ExgS and EngK brought about a synergistic effect on decomposition of ASC, and high cellulase activity due to significantly increased reducing sugar was detected.

Accordingly, with those results, it was confirmed that the recombinant ExgS and EngK did not exhibit the β-glucosidase activity, but high cellulase activity was exhibited by combining ExgS and EngK.

EXAMPLE 4

<Confirmation-2 of Synergistic Action of Enzymes>

1. Confirmation of Expression of Each of Enzymes ExgS, EngE, and EngK

Recombinant ExgS, EngE, and EngK were each expressed in E. coli serving as a host through the following steps 1) to 5).

1) exgS (SEQ ID NO: 1), engE (SEQ ID NO: 3), and engK (SEQ ID NO: 5) were each inserted into pCold-I (Takara Bio Inc.) serving as a vector for low-temperature expression, and gene-transferred to E. coli origami serving as a host for expression.

2) For the gene-transferred E. coli origami obtained in the above-mentioned section 1), colonies to which the genes were transferred respectively were subjected to screening by a colony direct PCR method, and inoculated into a 5-ml LB medium (supplemented with ampicillin (final concentration: 100 µg/ml)).

3) After the colonies to which the genes were transferred respectively obtained in the above-mentioned section 2) were each cultured at 37° C. for 10 hours, 1 ml of the culture solution was inoculated into a 500-ml 2×YT medium (supplemented with ampicillin (final concentration: 100 µg/ml)) and cultured with shaking at 140 rpm until it reached logarithmic growth phase ($OD_{600}$=0.5). After that, the temperature was rapidly cooled to 4° C. and retained for 30 minutes, and then, IPTG was added thereto so that the final concentration was 0.5 mM to induce protein expression, followed by incubation at 15° C. at 140 rpm for 24 hours.

4) Each of the bacteria in which protein expression was induced obtained in the above-mentioned section 3) was harvested by centrifugal precipitation (8,000×g, 4° C., 10 minutes), and suspended in 5 ml of a 50 mM potassium phosphate buffer (pH 6.3).

The suspension was subjected to sonication for about 300 seconds while cooled with ice so that the temperature did not rise. After the suspension was subjected to centrifugal precipitation (1,000×g, 3 minutes) and cellular fragments and the like was removed, centrifugal precipitation at 15,000×g was performed for 60 minutes to recover an insoluble fraction. A 0.1 mM Tris/HCl buffer (pH 7.4, 8 M urea) was added to pellets of the insoluble fraction and the precipitate was completely suspended by sonication, and then, incubation was performed at 4° C. for 24 hours to allow for denaturation and solubilization.

5) Each of the fractions obtained in the above-mentioned section 4) was subjected to SDS-PAGE, and CBB staining was used to confirm whether or not the target protein was present. As a result, it was confirmed that each of the proteins (ExgS, EngE, or EngK) was expressed mainly in the insoluble fraction.

2. Purification of Enzyme

For each of the enzymes, proteins that were not solubilized in 8 M urea (Wako Pure Chemical Industries, Ltd.) in the above-mentioned section 1 were removed by centrifugal precipitation (15,000×g, 60 min), and dialysis was performed at 4° C. for 24 hours using a regenerated cellulose membrane. In the dialysis, a refolding buffer (20 mM Tris/HCl, pH 7.0, 1.5 mM cellobiose (Wako Pure Chemical Industries, Ltd.) was exchanged four times.

Insolubilized proteins were removed by centrifugal precipitation (15,000×g, 60 min) again and a 10% streptomycin (Wako Pure Chemical Industries, Ltd.) solution (0.15 ml/ml) was added thereto. Incubation was performed at 4° C. for 1 hour, and then, the precipitate was removed by centrifugal precipitation (15,000×g, 60 min).

After that, the resultant was subjected to SDS-PAGE, and CBB staining and immunostaining were used to confirm whether or not the target protein was present. As a result, it was confirmed that purified proteins of the enzymes (ExgS, EngE, or EngK) were obtained.

3. Measurement of Enzyme Activity of ExgS, EngE, and EngK

The enzymes purified in the above-mentioned section 2 were mixed at various rates, and the presence or absence of a synergistic effect of enzyme activity for phosphoric acid swollen cellulose (acid swollen cellulose: ASC) prepared from crystalline cellulose Avicel (Merck Ltd.) was examined.

Specifically, 2.5 µl of 1 M $CaCl_2$, 175 µl of a 20 mM acetate buffer (pH 6.3, 2.5 mM $CaCl_2$), and 62.5 µl of ASC (cellulose content: 2%; final cellulose concentration: 0.5%) were put in a 1.5-ml tube and incubated at 37° C. for 20 minutes.

To this, 10 µl (final concentration: 1.6 mM) of each of mixed enzyme solutions prepared by mixing the enzymes purified in the above-mentioned section 2. in combination at a mixing rate of 100:0, 75:25, 50:50, 25:75, or 0:100 was added, and the mixture was incubated at 37° C. for 17 hours while being shaken at 140 rpm. Those rates were rates adjusted so that the final concentration of the enzymes was 1.6 mM given that the molecular weight (MW) of ExgS was 80.4 kDa, the molecular weight (MW) of EngE was 31.5 kDa, and the molecular weight (MW) of EngK was 97.1 kDa. After reaction for 17 hours, the enzyme reaction was terminated by heating at 100° C. for 5 minutes, and then, the amount of reducing sugar contained in the solution was measured by a DNS method in terms of cellobiose.

As a result, in the cases of combinations of ExgS and EngE, a combination of EngE and ExgS at a rate of 75:25 exhibited the highest synergistic effect (S25E75 in FIG. 6A) as shown in FIG. 6A. However, in the cases of combinations of EngE and EngK, substantially no synergistic effect was exhibited at any rate as shown in FIG. 6B. In addition, as shown in FIG. 6C, in the cases of combinations of ExgS and EngE, a combination of EngK and ExgS at a rate of 75:25 exhibited the highest synergistic effect (K75S25 in FIG. 6C).

Accordingly, with those results, it was confirmed that the enzyme activity was synergistically increased by combining ExgS and EngE or ExgS and EngK at an appropriate rate.

EXAMPLE 5

<Confirmation-3 of Synergistic Action of Enzymes>

Cellobiose is known as an enzyme activity inhibitor for exocellulase (cellobiohydrolase). Studies on CelS derived from *C. thermocellum* have been made and it is reported that its enzyme activity is decreased to 1/10 or less at a cellobiose concentration of 5%. Thus, the influence on a synergistic effect of enzyme activity of ExgS, EngE, and EngK was examined in the presence of cellobiose serving as an activity inhibitor.

Specifically, 2.5 µl of 1M $CaCl_2$, 18.25 µl of a 40 mM Tris/HCl buffer (pH 7.0), 2.5 mM $CaCl_2$, 0% or 0.5% cellobiose (FIG. 7: 0 mg/ml or 5.0 mg/ml)), and 62.5 µl of ASC (cellulose content: 2%; final cellulose concentration: 0.5%) were put in a 1.5-ml tube and the mixture was incubated at 37° C. for 20 minutes.

After that, 10 µl (final concentration: 1.6 mM) of each of mixed enzyme solutions prepared by mixing ExgS, EngE, and EngK purified by the same manner as in the above-mentioned section 2. in Example 4 in combination at a mixing rate of 100:0, 75:25, 50:50, 25:75, or 0:100 were added thereto, and the mixture was incubated at 37° C. for 17 hours. Those rates were rates adjusted so that the final concentration of the enzymes was 1.6 mM given that the molecular weight (MW) of ExgS was 80.4 kDa, the molecular weight (MW) of EngE was 31.5 kDa, and the molecular weight (MW) of EngK was 97.1 kDa.

After reaction for 17 hours, the enzyme reaction was terminated by heating at 100° C. for 5 minutes, and then, the amount of reducing sugar contained in the solution was measured by a DNS method in terms of cellobiose.

Figure 7:
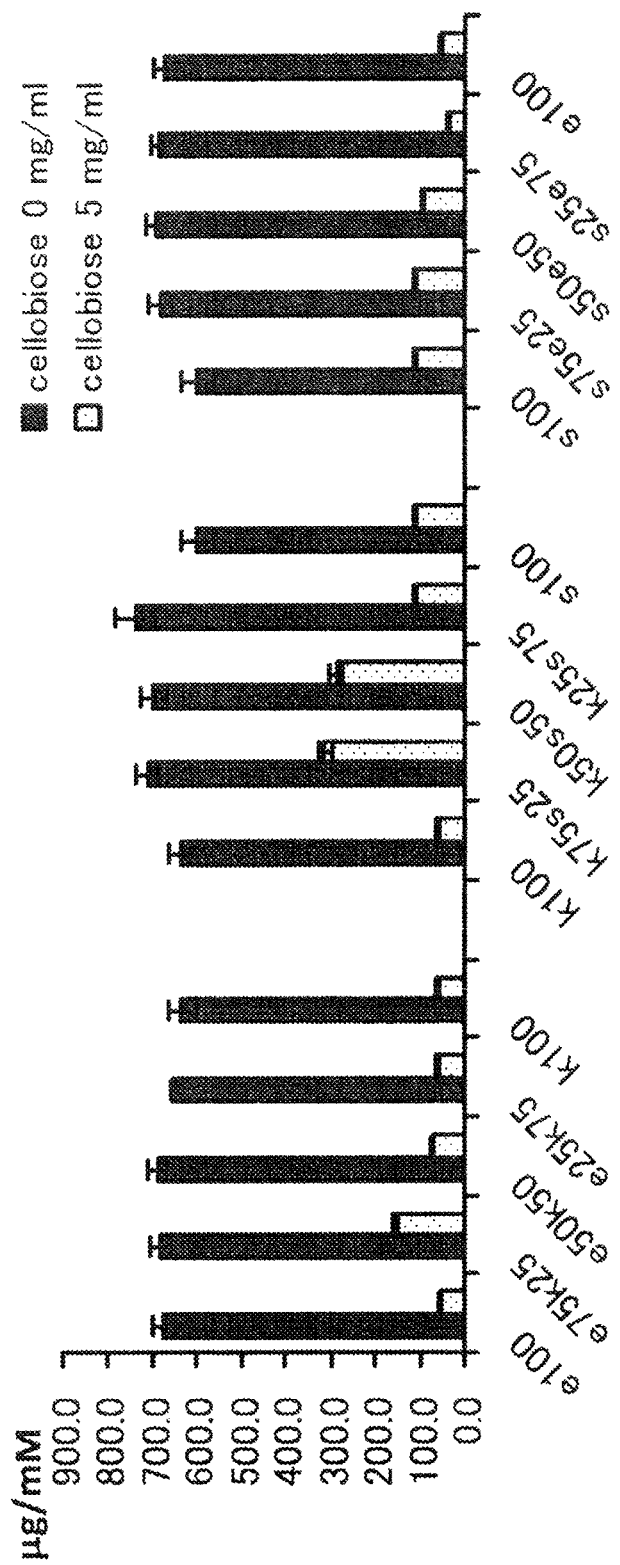
FIG. 7 is a graph showing results of synergistic action of enzymes in the presence of cellobiose (Example 5).

FIG. 7 shows the results. In this graph, the y-axis represents a rate between a cellobiose concentration in the reaction solution and a molar number of enzymes added and the x-axis represents enzymes added and the rate between the enzymes denoted by alphabets and numerical values, respectively. The alphabets s, e, and k in the x-axis represent ExgS, EngE, and EngK, respectively, and each of the subsequent numerical values represents a rate of an enzyme in enzymes added at 1.6 mM. For example, e75k25 means that EngE accounts for 75% and EngK accounts for 25% of the enzymes added at 1.6 mM.

Bar graphs are different in the initial cellobiose concentration in the reaction solution. The solid bars represent the cases in which the initial cellobiose concentration was 0 mg/ml and the dotted bars represent the cases in which the initial cellobiose concentration was 5 mg/ml.

Among those results, Table 3 shows cellobiose activity rates for the cases of adding each of the enzymes alone and for the cases of having an enzyme rate with particularly low activity inhibition by cellobiose (EngK:ExgS=75:25 or 50:50). As a result, it was confirmed that, in the cases of adding each of the enzymes alone, the activity decreased to 19%, 8%, and 10% in ExgS, EngE, and EngK, respectively and the cases suffered from comparable activity inhibition to CelS described above. However, in the cases of having a mixing rate of ExgS and EngK of 25:75 (k75s25 in FIG. 7) and 50:50 (k50s50 in FIG. 7), it was confirmed that the activity inhibition became moderate and high enzyme activity of 44% and 41% was maintained, respectively.

TABLE 3

| Enzyme | mixing rate (%) | activity (%) |
|---|---|---|
| EngE | 100 | 8 |
| EngK | 100 | 10 |
| ExgS | 100 | 19 |
| ExgS + EngK | 25 + 75 | 44 |
| ExgK + ExgS | 50 + 50 | 41 |

INDUSTRIAL APPLICABILITY

The soft biomass decomposition method of the present invention can be widely utilized as a soft biomass decomposition method using a simple procedure without pretreatment. Moreover, by incorporating the soft biomass decomposition method of the present invention as a step, it becomes easy to produce a useful substance such as ethanol from soft biomass. Further, it is also possible to provide an enzyme or group of enzymes capable of acting usefully in accordance with the type of soft biomass.

REFERENCE SIGNS LIST

Figure 2:
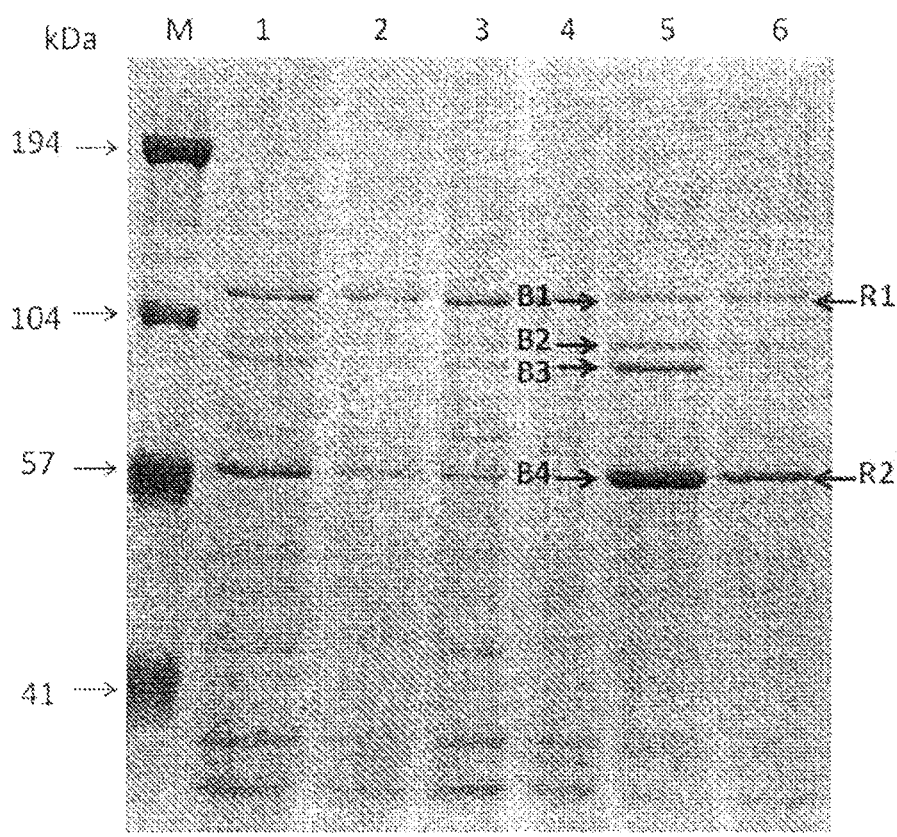
FIG. 2 is an image showing results of SDS-PAGE (Example 2).

[FIG. 2]
M: Protein marker
1: Supernatant fraction of *C. cellulovorans* culture supernatant (substrate: bagasse)
2: Supernatant fraction of *C. cellulovorans* culture supernatant (substrate: rice straw)
3: Non-adsorbed fraction (substrate: bagasse)
4: Non-adsorbed fraction (substrate: rice straw)
5: Adsorbed fraction (substrate: bagasse)
6: Adsorbed fraction (substrate: rice straw)
B1, B2, B3, B4, R1, R2: Cut band portion
[FIGS. 3]
M: Prestained SDS-PAGE standards
b: bglA gene containing transformant
S: exgS gene containing transformant
K: engK gene containing transformant

Figure 6:
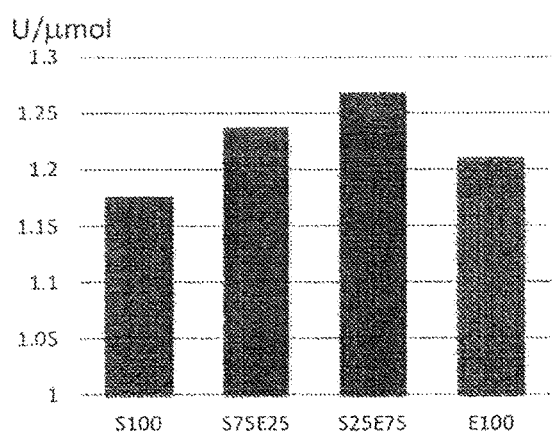
FIG. 6 are graphs showing results of synergistic action of enzymes (Example 4).
Figure 6:
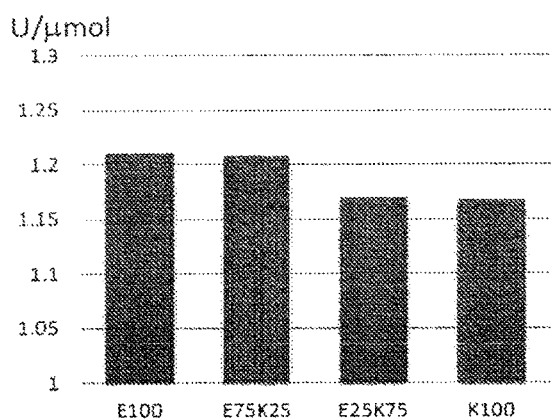
Figure 6:
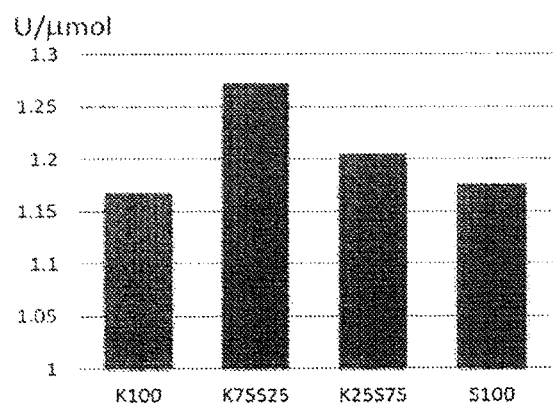

[FIG. 4]
b: bglA gene containing *E. coli* (origami) soluble fraction
S: exgS gene containing *E. coli* (origami) soluble fraction
K: engK gene containing *E. coli* (origami) soluble fraction
N1: 20-ml phosphate buffer (pH 7.4)
N2: *E. coli* (origami) soluble fraction
[FIG. 5]
ExgS: exgS gene containing *E. coli* (origami) soluble fraction
EngK: engK gene containing *E. coli* (origami) soluble fraction
ExgS+EngK: exgS gene containing *E. coli* (origami) soluble fraction+engK gene containing *E. coli* (origami) soluble fraction
Negative control: 20-ml phosphate buffer (pH 7.4)
[FIGS. 6]
A. S100: 100% of ExgS, S75E25: 75% of ExgS and 25% of EngE, S25E75: 25% of ExgS and 75% of EngE, E100: 100% of EngE
B. E100: 100% of EngE, E75K25: 75% of EngE and 25% of EngK, E25K75: 25% of EngE and 75% of EngK, K100: 100% of EngK
C. K100: 100% of EngK, K75S25: 75% of EngK and 25% of ExgS, K25S75: 25% of EngK and 75% of ExgS, S100: 100% of ExgS

The invention claimed is:

1. A method for producing ethanol from acid swollen cellulose, the method comprising:
   obtaining a decomposition product by contacting the acid swollen cellulose with an enzyme mixture of:
   an exocellulase comprising the amino acid sequence set forth in SEQ ID NO: 2, and
   a processive endocellulase comprising the amino acid sequence set forth in SEQ ID NO: 6,
   wherein a ratio of the exocellulase to the processive endocellulase in the enzyme mixture is from 25:75 to 50:50; and
   fermenting the decomposition product to obtain ethanol.

2. The method of claim 1, wherein fermenting the decomposition product is done using *C. cellulovorans* as a fermenting organism.

* * * * *

SEQUENCE LISTING

```
<160> NUMBER OF SEQ ID NOS: 7

<210> SEQ ID NO 1
<211> LENGTH: 2184
<212> TYPE: DNA
<213> ORGANISM: Clostridium cellulovorans

<400> SEQUENCE: 1
atgagaaaaa gattaaataa gatcgttgct gttgctttaa ctgcaacaac tatatcatca      60
gtagcagcta ctgttaatac agctcaagtt tcagctgcac cagtagtgcc aaataatgag     120
tatgttcaac actttaagga tatgtacgct aagatccata atgcaaacaa tggatacttc     180
agtgatgaag gaataccttr tcacgcagtt gaaacattaa tggttgaagc accagactat     240
ggtcatgaaa ctacaagtga agctttcagt tactatatgt ggcttgaagc tatgaacgct     300
aagcttactg gagatttctc aggattcaaa aaagcttggg atgtaactga aaagtacata     360
attccaggtg agactgatca accaagcgca agtatgagca attatgatcc aaataagcca     420
gctacatatg cagctgaaca tccagatcca agcatgtacc catctcaatt acaatttggt     480
gctgctgtag gtaaggatcc attatacaat gaattaaaat ctacttatgg aactagccaa     540
gtatatggta tgcattggtt actagatgtt gataactggt atggttttgg tggtgcaaca     600
agcacaagcc cagtatacat caacactttc caaagaggtg ttcaagaatc ttgttgggaa     660
actgtgccac aaccatgtaa agacgaaatg aagtacggtg gaagaaacgg tttcttagat     720
ctattcactg gtgattcaca atacgcaact caatttaaat atactaacgc tccagacgca     780
gatgctcgtg cagttcaagc tacttactat gcacaattag ctgctaaaga atggggagta     840
gacatcagct catatgtagc aaaatctact aagatgggtg acttcttaag atattcattc     900
tttgataaat actttagaaa agttggaaat tcaacacaag caggaactgg atatgattca     960
gctcaatacc tattaaactg gtactatgct tggggtggtg aatcagctc aaactggtct    1020 tggagaattg gatcaagcca taaccatttc ggataccaaa acccaatggc agcatggata    1080
```

```
ttatcaaata catctgactt taaaccaaag tcaccaaatg ctgctacaga ttggaataac    1140
agtttaaaga gacaaataga attctatcaa tggttacaat ctgctgaagg tggtatcgct    1200
ggaggagcta gtaactcaaa tggaggaagc tatcaagcat ggccagcagg tactgcaaca    1260
ttctacggaa tgggatatac tcctcaccca gtatacgaag atccaggtag taacgaatgg    1320
tttggtatgc aagcatggtc aatgcaacgt gtggctgaat actactacag ttcaaaagat    1380
ccagcagcta aatcattact tgataaatgg gctaaatggg cttgtgcaaa tgttcaattc    1440
gatgatgcag ctaagaaatt taagattcct gctaaattag tatggactgg acaaccagat    1500
acttggactg gatcatatac aggaaaattc aatcttcatg ttaaagttga agcttatgga    1560
gaagatcttg gagtagcagg ttcactttct aatgcattat catattatgc aaaagctctt    1620
gaatctagca cagatgctgc agataaagta gcatataaca ctgcaaaaga aacttctaga    1680
aagatacttg attacttatg ggcaagctac caagatgata agggtatagc agttactgaa    1740
acaagaaatg atttcaaacg tttcaatcaa tctgtatata ttccatcagg ttggacagga    1800
aaaatgccta atggagatgt aatccaaagt ggagctactt tcttaagcat acgttcaaaa    1860
tacaaacaag atccatcatg gccaaaagtt gaagctgctt tagcaaatgg tactggtgtt    1920
gatatgacat accacagatt ctggggtcaa agtgatatcg ctatagcatt tggaacatac    1980
ggtacattat tcacagaccc tactccagga ttaaaaggtg atgttaactc tgatgctaaa    2040
gtaaatgcta tagatttagc tatattaaag aaatacatct tagattcaac aactaaaatt    2100
aacactgcta attctgatat gaacggtgat ggaaaagtta atgcaatgga tttagcttta    2160
ttaaagaaag cacttcttgc ttaa                                          2184

<210> SEQ ID NO 2
<211> LENGTH: 727
<212> TYPE: PRT
<213> ORGANISM: Clostridium cellulovorans

<400> SEQUENCE: 2

Met Arg Lys Arg Leu Asn Lys Ile Val Ala Val Ala Leu Thr Ala Thr
1               5                   10                  15

Thr Ile Ser Ser Val Ala Ala Thr Val Asn Thr Ala Gln Val Ser Ala
            20                  25                  30

Ala Pro Val Val Pro Asn Asn Glu Tyr Val Gln His Phe Lys Asp Met
        35                  40                  45

Tyr Ala Lys Ile His Asn Ala Asn Asn Gly Tyr Phe Ser Asp Glu Gly
    50                  55                  60

Ile Pro Tyr His Ala Val Glu Thr Leu Met Val Glu Ala Pro Asp Tyr
65                  70                  75                  80

Gly His Glu Thr Thr Ser Glu Ala Phe Ser Tyr Tyr Met Trp Leu Glu
                85                  90                  95

Ala Met Asn Ala Lys Leu Thr Gly Asp Phe Ser Gly Phe Lys Lys Ala
            100                 105                 110

Trp Asp Val Thr Glu Lys Tyr Ile Ile Pro Gly Glu Thr Asp Gln Pro
        115                 120                 125

Ser Ala Ser Met Ser Asn Tyr Asp Pro Asn Lys Pro Ala Thr Tyr Ala
    130                 135                 140

Ala Glu His Pro Asp Pro Ser Met Tyr Pro Ser Gln Leu Gln Phe Gly
145                 150                 155                 160

Ala Ala Val Gly Lys Asp Pro Leu Tyr Asn Glu Leu Lys Ser Thr Tyr
                165                 170                 175
```

```
Gly Thr Ser Gln Val Tyr Gly Met His Trp Leu Leu Asp Val Asp Asn
            180                 185                 190
Trp Tyr Gly Phe Gly Ala Thr Ser Thr Ser Pro Val Tyr Ile Asn
        195                 200                 205
Thr Phe Gln Arg Gly Val Gln Glu Ser Cys Trp Glu Thr Val Pro Gln
    210                 215                 220
Pro Cys Lys Asp Glu Met Lys Tyr Gly Gly Arg Asn Gly Phe Leu Asp
225                 230                 235                 240
Leu Phe Thr Gly Asp Ser Gln Tyr Ala Thr Gln Phe Lys Tyr Thr Asn
                245                 250                 255
Ala Pro Asp Ala Asp Ala Arg Ala Val Gln Ala Thr Tyr Tyr Ala Gln
            260                 265                 270
Leu Ala Ala Lys Glu Trp Gly Val Asp Ile Ser Ser Tyr Val Ala Lys
        275                 280                 285
Ser Thr Lys Met Gly Asp Phe Leu Arg Tyr Ser Phe Phe Asp Lys Tyr
    290                 295                 300
Phe Arg Lys Val Gly Asn Ser Thr Gln Ala Gly Thr Gly Tyr Asp Ser
305                 310                 315                 320
Ala Gln Tyr Leu Leu Asn Trp Tyr Tyr Ala Trp Gly Gly Ile Ser
                325                 330                 335
Ser Asn Trp Ser Trp Arg Ile Gly Ser Ser His Asn His Phe Gly Tyr
            340                 345                 350
Gln Asn Pro Met Ala Ala Trp Ile Leu Ser Asn Thr Ser Asp Phe Lys
        355                 360                 365
Pro Lys Ser Pro Asn Ala Ala Thr Asp Trp Asn Asn Ser Leu Lys Arg
    370                 375                 380
Gln Ile Glu Phe Tyr Gln Trp Leu Gln Ser Ala Glu Gly Gly Ile Ala
385                 390                 395                 400
Gly Gly Ala Ser Asn Ser Asn Gly Gly Ser Tyr Gln Ala Trp Pro Ala
                405                 410                 415
Gly Thr Arg Thr Phe Tyr Gly Met Gly Tyr Thr Pro His Pro Val Tyr
            420                 425                 430
Glu Asp Pro Gly Ser Asn Glu Trp Phe Gly Met Gln Ala Trp Ser Met
        435                 440                 445
Gln Arg Val Ala Glu Tyr Tyr Tyr Ser Ser Lys Asp Pro Ala Ala Lys
    450                 455                 460
Ser Leu Leu Asp Lys Trp Ala Lys Trp Ala Cys Ala Asn Val Gln Phe
465                 470                 475                 480
Asp Asp Ala Ala Lys Lys Phe Lys Ile Pro Ala Lys Leu Val Trp Thr
                485                 490                 495
Gly Gln Pro Asp Thr Trp Thr Gly Ser Tyr Thr Gly Asn Ser Asn Leu
            500                 505                 510
His Val Lys Val Glu Ala Tyr Gly Glu Asp Leu Gly Val Ala Gly Ser
        515                 520                 525
Leu Ser Asn Ala Leu Ser Tyr Tyr Ala Lys Ala Leu Glu Ser Ser Thr
    530                 535                 540
Asp Ala Ala Asp Lys Val Ala Tyr Asn Thr Ala Lys Glu Thr Ser Arg
545                 550                 555                 560
Lys Ile Leu Asp Tyr Leu Trp Ala Ser Tyr Gln Asp Lys Gly Ile
                565                 570                 575
Ala Val Thr Glu Thr Arg Asn Asp Phe Lys Arg Phe Asn Gln Ser Val
            580                 585                 590
Tyr Ile Pro Ser Gly Trp Thr Gly Lys Met Pro Asn Gly Asp Val Ile
```

```
                595                 600                 605
Gln Ser Gly Ala Thr Phe Leu Ser Ile Arg Ser Lys Tyr Lys Gln Asp
        610                 615                 620

Pro Ser Trp Pro Asn Val Glu Ala Ala Leu Ala Asn Gly Thr Gly Val
625                 630                 635                 640

Asp Met Thr Tyr His Arg Phe Trp Gly Gln Ser Asp Ile Ala Ile Ala
                645                 650                 655

Phe Gly Thr Tyr Gly Thr Leu Phe Thr Asp Pro Thr Pro Gly Leu Lys
        660                 665                 670

Gly Asp Val Asn Ser Asp Ala Lys Val Asn Ala Ile Asp Leu Ala Ile
            675                 680                 685

Leu Lys Lys Tyr Ile Leu Asp Ser Thr Thr Lys Ile Asn Thr Ala Asn
        690                 695                 700

Ser Asp Met Asn Gly Asp Gly Lys Val Asn Ala Met Asp Leu Ala Leu
705                 710                 715                 720

Leu Lys Lys Ala Leu Leu Ala
                725
```

<210> SEQ ID NO 3
<211> LENGTH: 3093
<212> TYPE: DNA
<213> ORGANISM: Clostridium cellulovorans

<400> SEQUENCE: 3

```
atgaagaaga gaaacagaat actatcattt ttgctagttt tagcaatggt attctcttgt      60
gttgttagca accgttggt aaaagtatct gccgcagaag ctaactacac aacaaaaggc     120
actacgacac agatatatct tagtgccttt gcacaaaata ctgatgactg gcttggatg     180
agtatgggag atactgctag cttagtatat caagacgtaa caaatttcaa tgccatcgac     240
gctactagtg cctttgcaaa ggcaaatggt actgcaaact ttgggttaca ggttgttgat     300
ggaaatcttg ctgcaggaga aaaaagtaca ttaaaattcc atattggaac agttactatt     360
aaagcaactg gatataatga tgttgtggtt aatcttaaca aggattattc agaagcatat     420
gcagcagaaa aagtttcttg gggaatcaca ggaaacaata catcaatttt actaaatgat     480
tatttaccaa cagatgcagc agcgaaagca acgtatctac aaaagattac tagtgtaaaa     540
gcagatgtta cattatcaga atatcaattt gttaaaccag catcaactgg gtcaacttct     600
gaaagtgtat actcatcagg tgatgcaaca aagatttatg ctagtgcgtt tgcacaaaat     660
actgatgact gggcttggat gagcatggga gatactgctg ttttaacata tcaaactgct     720
acaaacgtaa atgctatcaa tgcaggtact gcatttgcaa gtgcaaatgg aactgcaaac     780
tttggtatcc aaattgttga cggaaaccta gctgctgcag aaaaaatgac ttggggactt     840
actggaaata acacacaaat tttattaaat agttatttac aacggatgc aactgcaaaa     900
gctgcatatc tacaaaaaat aacttctgtt acagctgatg ttacagtaac agattatcaa     960
tcgattaaac cagcaacagc aactggggaa gttctttaca acaccagg tgttgaaaca    1020
aagatttctg ctagtgcttt tgcacaaaac accgatgact gggcttggat gagcgtaggt    1080
gatggtgtta gtcttcaata tcaaactgat acaactttaa atgctattag tgctgctggt    1140
acattagcaa aagcaaatgc tacagcaaac tttggtataa atattgttga tggaaatctt    1200
gctgctggag atgcaaacac attaaagttc catgttggaa cagttacaat taaagcaaca    1260
ggttatgatg accttgtgat taacttaaat aaagattact cagaagcatt tgcagcagaa    1320
aaagcttctt ggggacttac aggaaacaca aaacaaattt tattaaactc ttatttacca    1380
```

```
acagatgcaa cagcaaaagt aaactatctt caaaaggtta ctagtgttac agctgatgta      1440
aaagtaacag attatacgtt tattaaatat gtaccaccag caccagaatt ccctgctgat      1500
tacactcacc caacagaaat gagaggtctt tctgctatgg atttagtaaa agacatgaag      1560
attggttgga acttaggaaa tactttagaa tcagttggcg gagaaactgg ttggggtaat      1620
cctgtaacaa caaagaaaat gtttgataca ttaaaggcag ctggctttaa tacagttccg      1680
tattcagtaa gatgggatga aaactatatt gatgctaatt atactattga tccagcatat      1740
atggctcgtg ttgaaacagt tgtaaactat gcacttgcta acgatatgta tgccattgtt      1800
aatattcacc ataataaatt ccaaggtcaa tttgatgaag cacacaaagc tgccatcatt      1860
aacgaaggta ctattgtatg gactcaaatt gcaaccact ttaaagatta tagtgataaa       1920
ttaatatttg atacaataaa tgaaccaaga catgaagaag actgggttgg tacttcagaa      1980
tactttaatg tcttaaatga atataacgca aaaatagttc ctgtaatacg tgcaactggc      2040
gaaaataatg ctaagagact tataatggtt cctacttatt gtgcttcttc agattatcct      2100
aaggttgctg gtatggtagt accaaatgat cctaatgttg cagtatctat ccacgcttac      2160
ataccatata atttagcact taatatagct ccaggtacac caactacctt tggtgatgct      2220
gacgcagcat ttattgacaa gactttcaga atgttaaaca cacatttgt taaaaaggga       2280 attcctgtta ttatcggtga attcgcgatt acagataaag ataacttaca agacagaatt      2340
aactttacga agttctatgt atcaacagct actgcttatg gaatgccatg tttgtggtgg      2400
gataataata attttggtag cacaggtgag agactggggc ttttaaatag aaaaaacctt      2460
acattccctt atcctgaatt agtacaagct atgaaagatg gtttcaacaa tccaagagat      2520
ctttcaaccg ttgatccaaa cgtattattt agtggtacag catcttgtac aggctggagc      2580
acagcacttt cattatccta tggcttagat tttgtagata ctgaattac aaatgatttt       2640 acaatagctg tagattacac aagtgaaaat gtacctcaat tagtcctata tggaaacttg      2700
actggtacag gttgggttat ggtaaaacct tcaacaatca aaacaagcgc aactacaaag      2760
actgcatact ttactataaa tgatatggta agtgcatata agaaagctct tgcaaactat      2820
gatagctatg gtaaggtatt accaggaatc caaggtattt tagttggaga tactggtgca      2880
gaccttacag taacaaaagt ttacaagaat gcacaacctg taaatcttct aggcgatgta      2940
gacggtaatg atgtagttaa ttcacttgat tttgagttat taaagaagta tgtattaaac      3000
aatgatacaa tgataaacaa agctagtgca gatttaaata aggatggaaa atcaacata      3060 attgatcttg cattcttaaa aaaagcaata taa                                    3093
```

<210> SEQ ID NO 4
<211> LENGTH: 1030
<212> TYPE: PRT
<213> ORGANISM: Clostridium cellulovorans

<400> SEQUENCE: 4

```
Met Lys Lys Arg Asn Arg Ile Leu Ser Phe Leu Leu Val Leu Ala Met
1               5                   10                  15

Val Phe Ser Cys Val Val Ser Lys Pro Leu Val Lys Val Ser Ala Ala
                20                  25                  30

Glu Ala Asn Tyr Thr Thr Lys Gly Thr Thr Thr Gln Ile Tyr Leu Ser
            35                  40                  45

Ala Phe Ala Gln Asn Thr Asp Asp Trp Ala Trp Met Ser Met Gly Asp
        50                  55                  60
```

```
Thr Ala Ser Leu Val Tyr Gln Asp Val Thr Asn Phe Asn Ala Ile Asp
 65                  70                  75                  80

Ala Thr Ser Ala Phe Ala Lys Ala Asn Gly Thr Ala Asn Phe Gly Leu
                 85                  90                  95

Gln Val Val Asp Gly Asn Leu Ala Ala Gly Glu Lys Ser Thr Leu Lys
            100                 105                 110

Phe His Ile Gly Thr Val Thr Ile Lys Ala Thr Gly Tyr Asn Asp Val
        115                 120                 125

Val Val Asn Leu Asn Lys Asp Tyr Ser Glu Ala Tyr Ala Ala Glu Lys
    130                 135                 140

Val Ser Trp Gly Ile Thr Gly Asn Asn Thr Ser Ile Leu Leu Asn Asp
145                 150                 155                 160

Tyr Leu Pro Thr Asp Ala Ala Lys Ala Thr Tyr Leu Gln Lys Ile
                165                 170                 175

Thr Ser Val Lys Ala Asp Val Thr Leu Ser Glu Tyr Gln Phe Val Lys
                180                 185                 190

Pro Ala Ser Thr Gly Ser Thr Ser Glu Ser Val Tyr Ser Ser Gly Asp
            195                 200                 205

Ala Thr Lys Ile Tyr Ala Ser Ala Phe Ala Gln Asn Thr Asp Asp Trp
    210                 215                 220

Ala Trp Met Ser Met Gly Asp Thr Ala Val Leu Thr Tyr Gln Thr Ala
225                 230                 235                 240

Thr Asn Val Asn Ala Ile Asn Ala Gly Thr Ala Phe Ala Ser Ala Asn
                245                 250                 255

Gly Thr Ala Asn Phe Gly Ile Gln Ile Val Asp Gly Asn Leu Ala Ala
            260                 265                 270

Ala Glu Lys Met Thr Trp Gly Leu Thr Gly Asn Asn Thr Gln Ile Leu
    275                 280                 285

Leu Asn Ser Tyr Leu Pro Thr Asp Ala Thr Lys Ala Ala Tyr Leu
    290                 295                 300

Gln Lys Ile Thr Ser Val Thr Ala Asp Val Thr Val Thr Asp Tyr Gln
305                 310                 315                 320

Ser Ile Lys Pro Ala Thr Ala Thr Gly Glu Val Leu Tyr Thr Thr Pro
                325                 330                 335

Gly Val Glu Thr Lys Ile Ser Ala Ser Ala Phe Ala Gln Asn Thr Asp
            340                 345                 350

Asp Trp Ala Trp Met Ser Val Gly Asp Val Ser Leu Gln Tyr Gln
    355                 360                 365

Thr Asp Thr Thr Leu Asn Ala Ile Ser Ala Ala Gly Thr Leu Ala Lys
370                 375                 380

Ala Asn Ala Thr Ala Asn Phe Gly Ile Asn Ile Val Asp Gly Asn Leu
385                 390                 395                 400

Ala Ala Gly Asp Ala Asn Thr Leu Lys Phe His Val Gly Thr Val Thr
            405                 410                 415

Ile Lys Ala Thr Gly Tyr Asp Asp Leu Val Ile Asn Leu Asn Lys Asp
        420                 425                 430

Tyr Ser Glu Ala Phe Ala Ala Glu Lys Ala Ser Trp Gly Leu Thr Gly
    435                 440                 445

Asn Thr Lys Gln Ile Leu Leu Asn Ser Tyr Leu Pro Thr Asp Ala Thr
    450                 455                 460

Ala Lys Val Asn Tyr Leu Gln Lys Val Thr Ser Val Thr Ala Asp Val
465                 470                 475                 480

Lys Val Thr Asp Tyr Thr Phe Ile Lys Tyr Val Pro Pro Ala Pro Glu
```

```
                485                 490                 495
Phe Pro Ala Asp Tyr Thr His Pro Thr Glu Met Arg Gly Leu Ser Ala
            500                 505                 510

Met Asp Leu Val Lys Asp Met Lys Ile Gly Trp Asn Leu Gly Asn Thr
        515                 520                 525

Leu Glu Ser Val Gly Gly Glu Thr Gly Trp Gly Asn Pro Val Thr Thr
    530                 535                 540

Lys Lys Met Phe Asp Thr Leu Lys Ala Ala Gly Phe Asn Thr Val Pro
545                 550                 555                 560

Tyr Ser Val Arg Trp Asp Glu Asn Tyr Ile Asp Ala Asn Tyr Thr Ile
                565                 570                 575

Asp Pro Ala Tyr Met Ala Arg Val Glu Thr Val Asn Tyr Ala Leu
            580                 585                 590

Ala Asn Asp Met Tyr Ala Ile Val Asn Ile His His Asn Lys Phe Gln
        595                 600                 605

Gly Gln Phe Asp Glu Ala His Lys Ala Ala Ile Ile Asn Glu Gly Thr
    610                 615                 620

Ile Val Trp Thr Gln Ile Ala Asn His Phe Lys Asp Tyr Ser Asp Lys
625                 630                 635                 640

Leu Ile Phe Asp Thr Ile Asn Glu Pro Arg His Glu Glu Asp Trp Val
                645                 650                 655

Gly Thr Ser Glu Tyr Phe Asn Val Leu Asn Glu Tyr Asn Ala Lys Ile
            660                 665                 670

Val Pro Val Ile Arg Ala Thr Gly Glu Asn Asn Ala Lys Arg Leu Ile
        675                 680                 685

Met Val Pro Thr Tyr Cys Ala Ser Ser Asp Tyr Pro Lys Val Ala Gly
    690                 695                 700

Met Val Val Pro Asn Asp Pro Asn Val Ala Val Ser Ile His Ala Tyr
705                 710                 715                 720

Ile Pro Tyr Asn Leu Ala Leu Asn Ile Ala Pro Gly Thr Pro Thr Thr
                725                 730                 735

Phe Gly Asp Ala Asp Ala Ala Phe Ile Asp Lys Thr Phe Arg Met Leu
            740                 745                 750

Asn Asn Thr Phe Val Lys Lys Gly Ile Pro Val Ile Ile Gly Glu Phe
        755                 760                 765

Ala Ile Thr Asp Lys Asp Asn Leu Gln Asp Arg Ile Asn Phe Thr Lys
    770                 775                 780

Phe Tyr Val Ser Thr Ala Thr Ala Tyr Gly Met Pro Cys Leu Trp Trp
785                 790                 795                 800

Asp Asn Asn Asn Phe Gly Ser Thr Gly Glu Arg Leu Gly Leu Leu Asn
                805                 810                 815

Arg Lys Asn Leu Thr Phe Pro Tyr Pro Glu Leu Val Gln Ala Met Lys
            820                 825                 830

Asp Gly Phe Asn Asn Pro Arg Asp Leu Ser Thr Val Asp Pro Asn Val
        835                 840                 845

Leu Phe Ser Gly Thr Ala Ser Cys Thr Gly Trp Ser Thr Ala Leu Ser
    850                 855                 860

Leu Ser Tyr Gly Leu Asp Phe Val Asp Thr Glu Phe Thr Asn Asp Phe
865                 870                 875                 880

Thr Ile Ala Val Asp Tyr Thr Ser Glu Asn Val Pro Gln Leu Val Leu
                885                 890                 895

Tyr Gly Asn Leu Thr Gly Thr Gly Trp Val Met Val Lys Pro Ser Thr
            900                 905                 910
```

```
Ile Lys Thr Ser Ala Thr Thr Lys Thr Ala Tyr Phe Thr Ile Asn Asp
    915                 920                 925

Met Val Ser Ala Tyr Lys Lys Ala Leu Ala Asn Tyr Asp Ser Tyr Gly
    930                 935                 940

Lys Val Leu Pro Gly Ile Gln Gly Ile Leu Val Gly Asp Thr Gly Ala
945                 950                 955                 960

Asp Leu Thr Val Thr Lys Val Tyr Lys Asn Ala Gln Pro Val Asn Leu
                965                 970                 975

Leu Gly Asp Val Asp Gly Asn Asp Val Val Asn Ser Leu Asp Phe Glu
                980                 985                 990

Leu Leu Lys Lys Tyr Val Leu Asn  Asn Asp Thr Met Ile  Asn Lys Ala
            995                1000                1005

Ser Ala  Asp Leu Asn Lys Asp  Gly Lys Ile Asn Ile  Ile Asp Leu
    1010                1015                1020

Ala Phe  Leu Lys Lys Ala Ile
    1025                1030

<210> SEQ ID NO 5
<211> LENGTH: 2679
<212> TYPE: DNA
<213> ORGANISM: Clostridium cellulovorans

<400> SEQUENCE: 5
atgcgtagta aaaaattaat agcttgcgta acagcattag ctacagtact aagtgtttca      60
acagttgcta cttcagttgc tactactaaa actgttagtg cagcaacaat ggtaagtgtt     120
ggagaattaa tcagaaacaa taaatttgac aatggtgttg ggttaccatg gacagttgtt     180
gagtcttacc cagcaaaatc tagctttgaa atcaaagatg gaaaatacta tgtaacagtt     240
cttcaagacg gtgtagaagg aagatgggat gttcaattcc gtcacagagg tcttgttata     300
gaacaaggac ataaatacag agttaaattt actgtaactg ctgataaaga ttgttacgtt     360
tatccaaaaa taggtgacca aggtgaacct tataaagaat attggaacta taactcatat     420
caaagagtac aattaagagc tggtgttcca acaacaattg atcaaacttt tgaaatgaga     480
gatgcaacag ctagaacagc tgaatttgca attcaccttg ctggtgactg taaggcagca     540
acattccctt atacatttac tttttgatgat atgtatgtat cagatccaca attcccagga     600
tatgtagctg aaactccaga accaacaaac gcaataagag ttaaccaagt aggttactta     660
ccaggcgtag caaagaaagc tacagttgtt acaaaagcaa caactccaat aaactggtac     720
ttaaagaata gttcaggtgt tcaagttgct actggcacaa caacagttaa aggcttagat     780
agcgcttcag agataatgt acatattata gatttctcaa attacacaac tccaggaact     840
ggctacacat tatcagttga ttcaacaaac gttgattcaa caattaatga ttctgcttca     900
agtatgcctt ttactatagg aacagattta tattctaaaa tgaaacatga atcaataaaa     960
tacttctact aaacagaag tgctattcca ataacaatgc catatgctga acgtactgat    1020
ttaactcgtg cagcaggaca tacaacggat ttgatgccaa ctgatgcaag ttcaagtgat    1080
ccaagtcctt ggtataaaga aaattatagt ctagatgtta caggtggatg gtatgacgct    1140
ggagaccacg gtaagtacgt tgttaacggt ggtatctctg tttggacaat gatgaaccaa    1200
tatgaaagag ctaagaaatt aggacaagct aatgtagctc catttgcaga taatacaatg    1260
aatatcccag aaagcggaaa cggctatcca gatattcttg atgaatcacg tttccaaatg    1320
gatttaatga tgaagatgca aattccagct ggtaaaactt acgctggtat ggctcaccat    1380
```

```
aaaggtcatg atgaaagatg acagctctt gcaatccgtc cagaccaaga tccaatgaaa    1440
cgttacttaa aagcaccaag tacagctgca acattaaacc ttgctgctac agctgcacaa    1500
gcttcacgtt tatggaaagg tattgatgat gcatattctg ctaagtgttt agcgtctgct    1560
gaaactgcat ggaaagcagc taaggctaat ccagcaatat atgcaccatt tgaaaatggt    1620
cctggtggtg gagcttacgg tgatgacaac gtaacagatg aattctactg ggcagcagca    1680
gaactttatg aaacaactgg aacatcagaa tatcttgact acatgaagaa taattcttca    1740
gataaattct taaagatgcc aactacatta actggtggag aagacaaagg attatcaggt    1800
gctttcgact ggggtaatgt tgctggttta ggaacaattt ctcttgctat tggtgataaa    1860
ttagatgcta catcaaaagc aactgtaaga gctaatgttg ctgccgctgc tgatgtatttt   1920 gtagctaata caaatagtga aggttatggt actccaatgg ttcaaggacc agcatttgag    1980
gaaaaggatg caagtggaaa agttataaga acaataactg gctatccatg gggttcaaac    2040
tcattcgtag ctaaccaagc tatcgttatg ggttacgctt atgactttac aaaaggcgat    2100
gcagataaga aaaaatctaa ttcgtacttt aatgggttaa caagtgctat ggactattta    2160
ttaggacgta acccaatggt acaatcatac gttactggat atggttctaa cccactagaa    2220
aatccacatc accgtttctg ggcataccaa gctgacaaca cattccctaa agctccagca    2280
ggatgtttat caggtggtcc taacacagga ttacaagatc catgggttaa aggctcaggt    2340
tggggagttg gtactaagcc agctgctaaa tgcttcatgg acaatataga atcatggtca    2400
actaatgaaa tcacaatcaa ctggaatgca ccaattgcat ggatgtcttc atacatggat    2460
ttaaataagg atgcaaaaac aatagatatt actattccac ctactacatc aggtgatgta    2520
aacggagata ctaagataaa tgctatcgat ttagctatgt taaagaaata tatcctagac    2580
aattcaactg taatcaaaac agctaacgct gatatgaata atgatggaaa aattaatgct    2640
atagatttag ctttattaaa gaagaaactt ctttcttaa                           2679

<210> SEQ ID NO 6
<211> LENGTH: 892
<212> TYPE: PRT
<213> ORGANISM: Clostridium cellulovorans

<400> SEQUENCE: 6

Met Arg Ser Lys Lys Leu Ile Ala Cys Val Thr Ala Leu Ala Thr Val
1               5                   10                  15

Leu Ser Val Ser Thr Val Ala Thr Ser Val Ala Thr Thr Lys Thr Val
                20                  25                  30

Ser Ala Ala Thr Met Val Ser Val Gly Glu Leu Ile Arg Asn Asn Lys
            35                  40                  45

Phe Asp Asn Gly Val Gly Leu Pro Trp Thr Val Glu Ser Tyr Pro
    50                  55                  60

Ala Lys Ser Ser Phe Glu Ile Lys Asp Gly Lys Tyr Tyr Val Thr Val
65                  70                  75                  80

Leu Gln Asp Gly Val Glu Gly Arg Trp Asp Val Gln Phe Arg His Arg
                85                  90                  95

Gly Leu Val Ile Glu Gln Gly His Lys Tyr Arg Val Lys Phe Thr Val
            100                 105                 110

Thr Ala Asp Lys Asp Cys Tyr Val Tyr Pro Lys Ile Gly Asp Gln Gly
        115                 120                 125

Glu Pro Tyr Lys Glu Tyr Trp Asn Tyr Asn Ser Tyr Gln Arg Val Gln
    130                 135                 140
```

-continued

Leu Arg Ala Gly Val Pro Thr Thr Ile Asp Gln Thr Phe Glu Met Arg
145                 150                 155                 160

Asp Ala Thr Ala Arg Thr Ala Glu Phe Ala Ile His Leu Ala Gly Asp
            165                 170                 175

Cys Lys Ala Ala Thr Phe Pro Tyr Thr Phe Thr Phe Asp Asp Met Tyr
            180                 185                 190

Val Ser Asp Pro Gln Phe Pro Gly Tyr Val Ala Glu Thr Pro Glu Pro
        195                 200                 205

Thr Asn Ala Ile Arg Val Asn Gln Val Gly Tyr Leu Pro Gly Val Ala
        210                 215                 220

Lys Lys Ala Thr Val Val Thr Lys Ala Thr Thr Pro Ile Asn Trp Tyr
225                 230                 235                 240

Leu Lys Asn Ser Ser Gly Val Gln Val Ala Thr Gly Thr Thr Thr Val
                245                 250                 255

Lys Gly Leu Asp Ser Ala Ser Gly Asp Asn Val His Ile Ile Asp Phe
            260                 265                 270

Ser Asn Tyr Thr Thr Pro Gly Thr Gly Tyr Thr Leu Ser Val Asp Ser
        275                 280                 285

Thr Asn Val Asp Ser Thr Ile Asn Asp Ser Ala Ser Ser Met Pro Phe
290                 295                 300

Thr Ile Gly Thr Asp Leu Tyr Ser Lys Met Lys His Glu Ser Ile Lys
305                 310                 315                 320

Tyr Phe Tyr Leu Asn Arg Ser Ala Ile Pro Ile Thr Met Pro Tyr Ala
                325                 330                 335

Glu Arg Thr Asp Leu Thr Arg Ala Ala Gly His Thr Thr Asp Leu Met
            340                 345                 350

Pro Thr Asp Ala Ser Ser Ser Asp Pro Ser Pro Trp Tyr Lys Glu Asn
        355                 360                 365

Tyr Ser Leu Asp Val Thr Gly Gly Trp Tyr Asp Ala Gly Asp His Gly
        370                 375                 380

Lys Tyr Val Val Asn Gly Gly Ile Ser Val Trp Thr Met Met Asn Gln
385                 390                 395                 400

Tyr Glu Arg Ala Lys Lys Leu Gly Gln Ala Asn Val Ala Pro Phe Ala
                405                 410                 415

Asp Asn Thr Met Asn Ile Pro Glu Ser Gly Asn Gly Tyr Pro Asp Ile
            420                 425                 430

Leu Asp Glu Ser Arg Phe Gln Met Asp Leu Met Met Lys Met Gln Ile
        435                 440                 445

Pro Ala Gly Lys Thr Tyr Ala Gly Met Ala His His Lys Gly His Asp
        450                 455                 460

Glu Arg Trp Thr Ala Leu Ala Ile Arg Pro Asp Gln Asp Pro Met Lys
465                 470                 475                 480

Arg Tyr Leu Lys Ala Pro Ser Thr Ala Ala Thr Leu Asn Leu Ala Ala
                485                 490                 495

Thr Ala Ala Gln Ala Ser Arg Leu Trp Lys Gly Ile Gly Asp Ala Tyr
            500                 505                 510

Ser Ala Lys Cys Leu Ala Ser Ala Glu Thr Ala Trp Lys Ala Ala Lys
        515                 520                 525

Ala Ser Pro Ala Ile Tyr Ala Pro Phe Glu Asn Gly Pro Gly Gly Gly
        530                 535                 540

Ala Tyr Gly Asp Asp Asn Val Thr Asp Glu Phe Tyr Trp Ala Ala Ala
545                 550                 555                 560

Glu Leu Tyr Glu Thr Thr Gly Thr Ser Glu Tyr Leu Asp Tyr Met Lys

```
                        565                 570                 575
Asn Asn Ser Ser Asp Lys Phe Leu Lys Met Pro Thr Thr Leu Thr Gly
                580                 585                 590

Gly Glu Asp Lys Gly Leu Ser Gly Ala Phe Asp Trp Gly Asn Val Ala
            595                 600                 605

Gly Leu Gly Thr Ile Ser Leu Ala Ile Gly Asp Lys Leu Asp Ala Thr
        610                 615                 620

Ser Lys Ala Thr Val Arg Ala Asn Val Ala Ala Ala Asp Val Phe
625                 630                 635                 640

Val Ala Asn Thr Asn Ser Glu Gly Tyr Gly Thr Pro Met Val Gln Gly
                645                 650                 655

Pro Ala Phe Glu Glu Lys Asp Ala Ser Gly Lys Val Ile Arg Thr Ile
                660                 665                 670

Thr Gly Tyr Pro Trp Gly Ser Asn Ser Phe Val Ala Asn Gln Ala Ile
            675                 680                 685

Val Met Gly Tyr Ala Tyr Asp Phe Thr Lys Gly Asp Ala Asp Lys Lys
        690                 695                 700

Lys Ser Asn Ser Tyr Phe Asn Gly Leu Thr Ser Ala Met Asp Tyr Leu
705                 710                 715                 720

Leu Gly Arg Asn Pro Met Val Gln Ser Tyr Val Thr Gly Tyr Gly Ser
                725                 730                 735

Asn Pro Leu Glu Asn Pro His His Arg Phe Trp Ala Tyr Gln Ala Asp
                740                 745                 750

Asn Thr Phe Pro Lys Ala Pro Ala Gly Cys Leu Ser Gly Gly Pro Asn
            755                 760                 765

Thr Gly Leu Gln Asp Pro Trp Val Lys Gly Ser Gly Trp Gly Val Gly
        770                 775                 780

Thr Lys Pro Ala Ala Lys Cys Phe Met Asp Asn Ile Glu Ser Trp Ser
785                 790                 795                 800

Thr Asn Glu Ile Thr Ile Asn Trp Asn Ala Pro Ile Ala Trp Met Ser
                805                 810                 815

Ser Tyr Met Asp Leu Asn Lys Asp Ala Lys Thr Ile Asp Ile Thr Ile
            820                 825                 830

Pro Pro Thr Thr Ser Gly Asp Val Asn Gly Asp Thr Lys Ile Asn Ala
        835                 840                 845

Ile Asp Leu Ala Met Leu Lys Lys Tyr Ile Leu Asp Asn Ser Thr Val
    850                 855                 860

Ile Lys Thr Ala Asn Ala Asp Met Asn Asn Asp Gly Lys Ile Asn Ala
865                 870                 875                 880

Ile Asp Leu Ala Leu Leu Lys Lys Lys Leu Leu Ser
                885                 890
```

<210> SEQ ID NO 7
<211> LENGTH: 1338
<212> TYPE: DNA
<213> ORGANISM: Clostridium cellulovorans

<400> SEQUENCE: 7

```
atggaaaagc taagatttcc caaagatttt attttggaa cagccactgc agcatatcaa      60
attgaaggag cttacaaaga agatgagaaa ggtgaatcta tttgggatag gtttagtcat     120
ataccaggaa atgtagctaa atgcataat ggtgatattg cttgtgatca ctatcataga     180
tataaagaag atgttcagct attaaaaagc cttggaatta aagttatag gttttcaatt     240 gcttggccta gaattttccc aaaaggttt ggcgagataa accagaaggg aattcagttc     300
```

```
tatagggatt taattgatga actaattaaa aatgatatag aaccagctat aacaatttat    360
cattgggatc ttccacaaaa gcttcaggat attggagggt gggcaaatcc gcaagttgct    420
gattactatg ttgattatgc aaacttatta ttcagagagt tcggagatag agtaaaaaca    480
tggataactc ataatgagcc atgggttgca tcatatcttg gctatgcttt aggagttcat    540
gctccaggaa ttaaagatat gaaaatggca ttgttagctg cacataacat attattatcg    600
cactttaagg cagttaaagc ttatagagaa ttagaacaag atgggcaaat aggtataaca    660
ttaaatcttt caacctgtta ttcaaattca gctgatgaag aagatattgc tgcagcccat    720
agaagtgatg gatggaacaa cagatggttt ttagatgctg cattaaaagg aacttatcct    780
gaggatatga taaaaatctt tagcgataca aatattatgc ctgaactacc taaagagtta    840
tttactgagg tatttgaaac ttctgatttt ttaggaataa attattatac acgacaagtt    900
gtaaagaata actctgaagc ttttatcggt gctgaaagtg tagcaatgga taatcctaaa    960
acagaaatgg gttgggagat atatccgcaa gggctttatg atttgctaac gaggatacac   1020
agggattatg ggaacataga tttatacata acagaaaacg gtgcagcttt taatgatatg   1080
gttaatagag acggtaaagt tgaagatgaa aatagattag attatttata cactcatttt   1140
gctgctgcat taagtgctat agaagcggga gtacctttaa agggatatta tatttggtct   1200
ttcatggata attttgagtg ggctgaagga tatgaaaaaa gatttggaat agtacatgta   1260
aactataaaa ctcaggagag aacaataaag aagagtgctt attggtataa ggagcttata   1320
gaaagatcta ataagtaa                                                 1338
```